(12) United States Patent
Andersen et al.

(10) Patent No.: US 11,058,782 B2
(45) Date of Patent: Jul. 13, 2021

(54) APPARATUS, METHOD, SYSTEM AND SOFTWARE PRODUCT FOR HAND SANITISATION

(71) Applicant: Scan Unie ApS, Copenhagen (DK)

(72) Inventors: Henrik Rasmus Andersen, Hellerup (DK); Jan Arlemark, Loulé (PT); Finn Jegård, Brøndby Strand (DK); Kenneth Francke, Copenhagen (DK); Jan Borgström, Saxtorp (SE)

(73) Assignee: SCAN UNIC APS, Copenhagen (DK)

( * ) Notice: Subject to any disclaimer, the term of this patent is extended or adjusted under 35 U.S.C. 154(b) by 0 days.

(21) Appl. No.: 16/354,083

(22) Filed: Mar. 14, 2019

(65) Prior Publication Data

US 2019/0209719 A1 Jul. 11, 2019

Related U.S. Application Data

(62) Division of application No. 15/542,927, filed as application No. PCT/DK2016/050012 on Jan. 15, 2016, now abandoned.

(30) Foreign Application Priority Data

Jan. 16, 2015 (GB) ....................................... 1500770
Oct. 7, 2015 (DK) ............................ PA2015 70628

(51) Int. Cl.
*A61L 2/18* (2006.01)
*A61L 2/00* (2006.01)
(Continued)

(52) U.S. Cl.
CPC ............. *A61L 2/0088* (2013.01); *A61L 2/183* (2013.01); *A61L 2/22* (2013.01); *A61L 2/24* (2013.01);
(Continued)

(58) Field of Classification Search
CPC .......... A61L 2/0088; A61L 2/183; A61L 2/24; A61L 2202/14; A61L 2202/17; B08B 3/08
See application file for complete search history.

(56) References Cited

U.S. PATENT DOCUMENTS 6,110,292 A 8/2000 Jewett et al.
6,236,953 B1 5/2001 Segal
(Continued)

FOREIGN PATENT DOCUMENTS

AU 2012232974 A1 4/2013
WO 97/45049 A1 12/1997
WO 2007/106888 A2 9/2007

OTHER PUBLICATIONS

English language abstract of "The effectiveness of ozonated water for hand washing before surgery"; Masui, Jun. 2001;50(6):672-5 (Year: 2001).*

(Continued)

*Primary Examiner* — Timothy C Cleveland
(74) *Attorney, Agent, or Firm* — Winston & Strawn LLP

(57) ABSTRACT

A method of implementing and using an apparatus (1*a*,1*b*, 13,25) to achieve hand sanitisation by application of ozone. The apparatus has a disinfecting chamber (3,3',110) with at least one port (2) adapted for insertion of at least one hand into the disinfecting chamber (3,110). A sensor (4) detects entry and/or exit of the hand (26) into the disinfecting chamber (3,110). An ozone water output (7,130) of an ozone water supply (8) is arranged to deliver ozone water to the at least one hand (26) when inserted into the disinfecting chamber (3,110). Control means (6) times start and stop of a discharge of ozone water from the at least one ozone water output (7,130) into the disinfecting chamber (3,110) when (Continued)

the at least one sensor (4) detects entry of the at least one hand (26) into the disinfecting chamber (3,110).

29 Claims, 9 Drawing Sheets

(51) Int. Cl.
    *A61L 2/22*     (2006.01)
    *A61L 2/24*     (2006.01)
    *B08B 3/08*     (2006.01)

(52) U.S. Cl.
    CPC .............. *B08B 3/08* (2013.01); *A61L 2202/14* (2013.01); *A61L 2202/17* (2013.01)

(56) References Cited

U.S. PATENT DOCUMENTS

| | | |
|---|---|---|
| 6,431,189 B1 | 8/2002 | Deibert |
| 2003/0156978 A1* | 8/2003 | Gillette .................. A23L 3/358 422/31 |
| 2012/0285825 A1 | 11/2012 | Benedetto |
| 2014/0186211 A1 | 7/2014 | Axelsen |

OTHER PUBLICATIONS

International Search Report and Written Opinion, Appl. No. PCT/DK2016/050012, dated Mar. 31, 2016.
International Preliminary Report on Patentability, Appl. No. PCT/DK2016/050012, dated Dec. 8, 2016.
Fujiwara et al., "Research Note: Effect of Ozonated Water Spray Droplet Size and Distance on the Dissolved Ozone Concentration at the Spray Target," Ozone: Science and Engineering, 2004, 26(5): 511-516 (Year: 2004).
U.S. Appl. No. 15/542,927, Restriction Requirement, dated Jan. 26, 2018.
U.S. Appl. No. 15/542,927, Non-Final Rejection, dated Mar. 2, 2018.
U.S. Appl. No. 15/542,927, Final Rejection, dated Jun. 20, 2018.
U.S. Appl. No. 15/542,927, Advisory Action, dated Sep. 11, 2018.
U.S. Appl. No. 15/542,927, Non-Final Rejection, dated Nov. 20, 2018.
U.S. Appl. No. 15/542,927, Final Rejection, dated Feb. 15, 2019.

* cited by examiner

APPARATUS, METHOD, SYSTEM AND SOFTWARE PRODUCT FOR HAND SANITISATION

CROSS-REFERENCE TO RELATED APPLICATIONS

The present application is a division of U.S. application Ser. No. 15/542,927 filed Jul. 11, 2017, which is a 371 filing of International patent application no. PCT/DK2016/050012 filed Jan. 15, 2016, which claims the benefit of each of British application no. 1500770.1 filed Jan. 16, 2015 and Danish application no. PA 2015 70628 filed Oct. 7, 2015.

FIELD OF THE INVENTION

The present invention relates to the field of sanitisation of skin, in particular to an apparatus and a system for hand sanitisation by application of ozone water. Moreover, the present invention concerns a standardised method of hand sanitisation including disinfection. Furthermore, the present invention relates to software products recorded on machine-readable data storage media, wherein the software products are executable on computing hardware for implementing aforesaid method.

BACKGROUND OF THE INVENTION

Implementation of hygiene is one of the most important actions in fields and areas where a proliferation of pathogens and other microorganisms would threaten health. Where an environment is accessible by many people, such as public facilities or areas, the concept of hygiene becomes even more important. Obvious examples include a hospital or other medical institution, a nursing home, an airport, a hotel, a veterinary practice, or even a place where food is being prepared.

Infections, frequently caused by microorganisms and resulting from poor hygiene, have far reaching consequences beyond mere inconvenience to the affected individual. Associated costs in terms of required medical response and impact on working time lost, and the associated risk to third parties exposed to such infections, must be taken into account. In some environments, such as a hospital, the proliferation of infection can become a significant danger. An individual with a poor immune capability, especially someone who is already sick, is particularly badly equipped to deal with additional infection. Cross contamination of infections between patients is a particular hazard.

The transmission of microorganisms is known to be amplified by lack of hygiene. In particular, hands are known to be a very likely transmission medium, especially for the transmission of disease-causing pathogens, e.g. bacteria, and micro-pollutants. Thus by targeting hand hygiene, an effective improvement can be made in the reduction of transmission.

Cleanliness of hands is often implemented by means of a hand wash with soap and/or the use of an antibacterial treatment, such as an alcohol for disinfecting purpose. An antibacterial agent applied to living tissue, organism or object to destroy microorganisms is generally known as an antiseptic and that applied to non-living tissue or object, a disinfectant. A hand antiseptic, hand disinfectant, or hand sanitiser agent is a supplement or alternative to hand washing with soap and water. The alcohol is used briefly as a terminal brief cleaning step when the individual leaves the toilet facilities and the alcohol is rarely spread over the entire area of the hand to an extent that is 100% effective to kill microorganisms and vira.

Said washes with soap, even if carried out thoroughly over an extended period of time, have a relatively poor degree of success. Such a method is also highly dependent on the individual's implementation and cannot be relied upon to be completely reproducible each time a wash is undertaken. One of the most frequent causes of bad hand hygiene is that individuals simply cut time for washing and subsequent after treatment, e.g. using an antiseptic, such as disinfecting by alcohol. They become impatient and do not use sufficient time for the process to get a good and standardised sanitisation result wherein pathogenics and other kinds of microorganisms are destructed.

Further, the individual may be discouraged from extensive washing due to a number of possible side-effects of the wash process on the skin, such as allergy, rash, dryness and the triggering of medical conditions e.g. psoriasis. This is especially of concern among individuals who are required to wash their hands frequently to perform procedures many times in quick succession, e.g. a nurse who must wash hands between treating different patients. In extreme cases, the consequences of the washing process may affect the individual to such an extent that he/she is unable to continue to perform the tasks required in their work for a period.

Alternative sanitising methods rely on UV (ultraviolet) systems, which produce radiation to kill microorganisms. Many of these systems do not produce adequate radiation to perform the task of removing e.g. bacteria and spores within an acceptable time. Thus the skin is not adequately cleaned and/or disinfected. Further, exposing skin to such radiation can lead to burns and it may be inadvisable to do so for frequent long-term use. The UV method is therefore more often applied to sterilise air, in hospitals for example.

More sophisticated sanitisation means comprise the use of ozone as a chemical to target e.g. organic compounds and microorganisms. Ozone oxidises most or all organic compounds, aromatic- and unsaturated-hydrocarbons, acting as a biocide effective for killing e.g. bacteria, moulds, spores, fungi. However, it is not fully comprehensive in effect: saturated hydrocarbons and some kinds of compounds or chemicals may or may not react with ozone. Ozone is a chemically aggressive substance, with a high activity, and which decomposes relatively quickly leaving little residue. It is frequently used for disinfecting water, surfaces and even food.

In combination with water, ozone has been used for hand disinfection, applied in some cases simply as ozonated water. Examples of such implementations can be found in patent documents, such as Japanese patent document JP1993000043294 (1993), Chinese patent document CN 201020281922 (2010), and United States patent document U.S. Ser. No. 08/619,042 (1996). In particular, U.S. Ser. No. 13/555,512 (2012) discloses an optional addition of ozone to a nebulised solution containing active chlorine comprised in a hand washing and disinfection apparatus, wherein the washing medium is presented to the hands in the form of a mist. Despite its high chemical activity, ozone is considered advantageous for hand sanitisation as it is considered to be less damaging to skin than other sanitizing agents. Among other things, it is effective for the removal of bacteria, viruses, microorganisms, fungi, pathogens, spores, allergens and some pollutants, including chemicals. Ozone acts on the cell wall of pathogens by reaction with the constituent organic molecules.

The abstract of "The effectiveness of ozonated water for hand washing before surgery" (Department of Anesthesia, Southern Tohoku General Hospital, Southern Tohoku Research Institute for Neuroscience, Koriyama 963-8563. Masui. The Japanese journal of anesthesiology July 2001; 50(6):672-5. Isosu T, Kan K, Hayashi T, Fujii M) reports the investigation of the effectiveness of ozonated water as a disinfectant for hand washing before surgery. The effectiveness of using 4 ppm of ozonated water, which is expected to have a short-term bactericidal effect, and 0.2% benzalkonium chloride/83% ethanol solution, which is expected to have a long-term bactericidal effect, was compared with that of the conventional hand-washing method (Furbringer's method using a scrubbing agent containing povidone-iodine). Contrary to expectations the results showed no significant differences in the numbers of live bacteria and exponential reduction rates in live bacteria, indicating that the tested sanitisation technique with ozonated water should be improved.

United States patent document U.S. Pat. No. 6,236,953 discloses a system for monitoring use of a hand sink to determine compliance with a cleansing regime by a user. A monitor box next to the hand sink includes a data collection device for determining the identity of the user of the apparatus during each use for comparison to predetermined operating parameters, and for determining whether the user has completed the predetermined sequence. Compliance with the operating parameters by the user is evaluated based on the determined identity of the user and the sequence completion information. A water dechlorinator is positioned upstream a mixing union for the hot and cold water lines, and a water ozonator is positioned upstream from the mixing union on one of the water lines, so that ozonated water runs out of the tap into the wide open sink.

When using the system of U.S. Pat. No. 6,236,953 the user needs to rub the hands against each other as in any ordinary hand washing process with soap. Thus this known system has no solution to standardize the sanitisation process. Rather in U.S. Pat. No. 6,236,953 compliance is obtained by allotting a use regime to a specific user of how often to repeat handwash using ozonated water. So the system of U.S. Pat. No. 6,236,953 simply uses ozonated water as replacement for tap water to perform a single step handwash.

Another patent related to the above is United States patent document US20020019709 which also relates to a system for controlling operation of a sink. This system includes a valving device adapted to be coupled to plumbing of the sink to selectively allow water to flow into a basin of the sink, and has means for monitoring and controlling operation of the sink. A water treatment device, such as a water dechlorinator located upstream from a mixing union or a water ozonator located upstream from the mixing union, may be coupled to the plumbing assembly of the sink. This configuration provides a flow of dechlorinated, ozonated water to a sink via the tap as in U.S. Pat. No. 6,236,953. As in U.S. Pat. No. 6,236,953 the user needs to rub the hands against each other and move the hands around below the running ozonated tap water to complete the hand wash. This procedure is not, and cannot, serve to standardize the physical action of the handwashing and the disinfection to the extent that all areas of the hands get the highest possible degree of sanity action.

U.S. Pat. No. 6,431,189 relates to a disinfecting apparatus wherein a disinfecting chemical solution is sprayed over the hands.

Australian patent application AU2012232974 relates to an apparatus for automated hand washing. The device is a hand washer-dryer with a chamber for rinsing the hands. This known apparatus utilizes water sterilised with ozone to rinse the hands by application of atomised sterilised water over the hand after the hands have been rinsed with soap.

A drawback of the current ozone implementations, however, is that the sanitising process is not always efficient, in particular because different individuals do not perform this process the same way and use too little time and effort so treat the entire hand.

Accordingly, a main aspect of the present invention is to provide an improved alternative to the prior art sanitisation apparatuses and systems.

It is yet an aspect of the present invention to provide an alternative apparatus and method for disinfecting hands after the hand washing has been completed.

It is yet an aspect of the present invention to provide an apparatus and method for disinfecting hands as a replacement for the conventional alcohol disinfection.

It is yet an aspect of the present invention to provide an apparatus and method for standardisation of the disinfection step of a hand cleaning procedure, which apparatus and method provide a higher level of sanitization than known devices and methods due to standardising in the near sanitisation environment.

It is yet an aspect of the present invention to provide an apparatus and method for disinfecting the whole area of the hands in a single well-defined action.

SUMMARY OF THE INVENTION

Accordingly, the present invention seeks to provide an improved sanitisation, including a sanitisation of hands in particular, however also sanitisation of elbows and forearm is among the body parts that can be disinfected by the sanitisation apparatus and method of the present invention.

Moreover, the present invention seeks to provide a safe, reliable and compact sanitisation apparatus suited to a broad spectrum removal of pathogens and contaminants. The pathogens and contaminants may comprise, but are not limited to, bacteria, viruses, fungi, microorganisms, pollutants, organic contaminants, non-organic contaminants. This list is not exhaustive.

The novel and unique whereby these and other aspects are achieved are embodied in a method and apparatus.

The method of hand sanitisation of the invention comprises the steps of:
sensing the introduction of the at least one hand of a user into a port or an ozone disinfecting chamber; and
sanitising the at least one hand by:
generating ozone water from an electrolytic ozone generator to provide electrolytically produced ozone dissolved in water, while operating the generator to provide ozone in the water at a concentration of 2 to 50 ppm;
delivering a gentle, low pressure flow of the ozone water to the disinfecting chamber from the electrolytic ozone generator at least one water output comprising to first and second ozone water delivery openings, and
wetting the hand with a continuous liquid flow of ozone water without an admixture with air to the first ozone water delivery openings which are arranged in a first pattern selected to deliver and spread a first flow of the liquid ozone water continuously over the palm of the inserted at least one hand, wherein said flow of ozone water is directed towards the palm to wet and disinfect all areas of the inserted at least one hand from above; and/or wetting the hand with a continuous liquid flow of ozone water without an admixture with air to the second ozone water delivery openings which are arranged in a second pattern selected to deliver and spread a second flow of the liquid ozone water continuously over the back of the inserted at least one hand, wherein said flow of ozone water is directed towards the back of the hand to wet and disinfect all areas of the inserted at least one hand from below.

The ozone disinfecting apparatus used in the method preferably includes control means which is arranged to start a discharge of ozone water from the ozone generator when the at least one hand is introduced into the disinfecting chamber and regulates timing of sanitization of the at least one hand inserted in the disinfecting chamber.

Additionally, the apparatus of the invention comprises a disinfecting chamber having
- at least one port adapted for insertion of at least one hand into said disinfecting chamber,
- at least one sensor adapted for detection of an entry and/or exit of the at least one hand into the disinfecting chamber,
- at least one ozone water output of an ozone water supply that comprises an electrolytic ozone generator (18) and being arranged to deliver ozone water to the at least one hand when inserted into the disinfecting chamber,
- a control means which
  - is arranged to start a discharge of ozone water from the at least one ozone water output into the disinfecting chamber when the at least one sensor detects entry of the at least one hand into the disinfecting chamber,
  - is arranged to stop the discharge of ozone water from the at least one ozone water output in response to an input from the control means,
  - comprises a timer arranged to cooperate with the at least one sensor to regulate a sanitisation timing of the at least one hand inserted in the disinfecting chamber,
  - wherein
    the at least one ozone water output of the disinfecting chamber comprises a first plurality of ozone water delivery openings arranged in a first pattern selected to deliver and spread a flow of ozone water over the palm of the inserted at least one hand, wherein said flow of ozone water is directed towards the palm to disinfect all areas of the inserted at least one hand from above, and/or a second plurality of ozone water delivery openings arranged in a second pattern selected to deliver and spread a flow of ozone water over the back of the inserted at least one hand to disinfect all areas of the inserted at least one hand from below.

Within the context of the present invention the term "plurality" means a plural in the sense of more than one.

The first plurality of ozone water delivery openings is advantageously arranged in a first pattern selected to spread the ozone water over the palm of the inserted at least one hand, and the second plurality of ozone water delivery openings is arranged in a second pattern selected to spread the ozone water over the back of the inserted at least one hand, so that the user needs not do anything else than just inserting the at least one hand via the port into the disinfecting chamber to disinfect all areas of the hand to same degree. So all of the fingers, including the fingertips, the fingernails and accompanying tissue between the fingers, the palm, and the back of the hand, and maybe even for some users a part of the wrist closest to the hand, the forearm and/or the elbow are disinfected without any efforts exerted to that aspect by the user in progress of being sanitised and during the sanitisation. The user simply holds the at least one hand still inside the disinfecting chamber and waits during the timed sanitisation cycle. The timer starts and stops the sanitisation in response to readings by the at least one sensor of the presence or non-presence of the hand inside the disinfecting chamber.

The patterns of the ozone water delivery openings can e.g. have a minimum outline corresponding to a left hand and a right hand, respectively, e.g. placed next to each other, and ozone water delivery openings covering the area defined by this outline. By restricting the users possibilities to move the hands into the port and inside the disinfecting chamber, and by providing the first plurality of ozone water delivery openings and the second plurality of ozone water delivery openings in patterns designed to extend over the at least one hand when the fingers are spread, and by the fact that the user keeps the at least one hand still in the same position and orientation during the sanitisation cycle this sanitisation cycle becomes the same every time,—thus the degree and time of sanitisation are controlled by the apparatus and the method. The user does not need to rub the hands to distribute a dispensed small amount of disinfecting alcohol to the extent possible before the alcohol evaporates on the skin or gets into all recesses of the hands. Instead the user is offered a novel standard disinfection of any area on the hand. The area of the port to the disinfecting chamber is kept as small as possible and much smaller than the opening of the sink basin. Besides from the narrow opening at the port the disinfecting chamber is closed on all sides thereby providing guidance for the individual user.

Preferably, the user washes his/her hand with a cleaning agent, such as soap, before proceeding to the sanitisation apparatus so as to make sure that larger particles etc. are removed so that the ozone water has a free passage to all of the hand areas, indents, webbings and nails included.

The port can e.g. be a slot for parallel insertion of the open hands. Thus the at least one port may conveniently be dimensioned for entry and/or exit of the at least one hand with an open palm but not with a clenched fist. The port to the disinfecting chamber is sized and shaped to limit the options of the user of how to make entry of the at least one hand into the disinfecting chamber. Only by making the at least one hand flat the user is able to insert a hand. The limited space inside the disinfecting chamber does not allow the user to close the hand to make a fist, nor to turn the hand one inserted. Instead the user keeps the hand with the fingers spread apart. If two hands are inserted these two hands are kept apart and preferably in minimum or no contact.

The at least one hand is kept out of direct contact with any interior face of the disinfecting chamber to allow the ozone water flowing out the first plurality of ozone water delivery openings and/or from the second plurality of ozone water delivery openings to contact and thoroughly disinfect all areas of the inserted at least one hand from above and/or from below.

The apparatus according to the present invention may further comprise a recognition device, arranged co-operative with the control means, suitable to detect and recognize at least one user whose at least one hand is to be sanitised and the control means further comprises means for storing data related to at least one sanitisation for the at least one user.

Advantageously, the recognition device gives the possibility of securing access for specific users, for allowing the apparatus to be used in a specific way tailored to a specific user (e.g. by running certain sanitisation operations dependent on who is using the apparatus and thereby tailoring levels of sanitisation to certain applications) and for enabling the logging of the use of the apparatus by a specific user or group of users. The recognition device may operate based on identification of a fingerprint, an eye scan, a badge or other security device comprising some kind of machine readable pattern, e.g. a barcode, or by a code input. A special user-specific sanitisation regime that includes recognition of the user is however not mandatory. The apparatus and method of the present invention can also operate without user recognition. In such embodiments the sanitation cycle, which is triggered by the at least one sensor senses the entry of the at least one hand, runs for a period predetermined in accordance to experience and tests to be satisfactory for an average user at the relevant location where the apparatus is operative.

The control means can advantageously further comprise means for storing data related to at least one sanitisation for the at least one user.

Accordingly, the means for storing data may comprise at least one sanitisation protocol arranged to be implemented for the at least one user.

By means of the timing aspect of this embodiment of the invention, an effective sanitisation protocol can be established, which comprises a disinfecting procedure implemented over an optimised and consistent timeframe for each user of the apparatus.

Advantageously, data storage also allows a record to be kept of apparatus function and implementation. It also provides an opportunity for a database to be developed and/or subsequent data analysis to be performed. Such data may comprise specific apparatus use data, including data associated with an individual user. The data logged in the data storage is a valuable means to identify bad habits of the user(s), to learn the user(s) to clean and disinfect hands, and finally but not least to design and target the sanitisation protocol(s). The data logged in the data storage is a valuable means for documentation of compliancy with hospitals policy or in connection with establishing contamination source and/or legal issues.

The at least one sanitisation protocol may advantageously be arranged to be implemented for the at least one user.

The at least one user can be a user unknown to the sanitisation protocol, a user known to the sanitisation protocol, or the user belongs to a group of users having a common sanitisation protocol. Advantageously, a specific apparatus usage can be controlled for a specific user. So within the scope of the present invention the sanitisation protocol can be customised to an individual user or to a group of users. Amongst other advantages this standardises the sanitisation process according to who is using the apparatus, which may be helpful to specify a level of cleanliness and sanitisation depending on the role that user performs.

Optionally, the ozone water supply comprises an electrolytic ozone generator.

The electrolytic ozone generator has a generator inlet connected to a water supply and at least one generator outlet connected to the first plurality of ozone water delivery openings and/or the second plurality of ozone water delivery openings of the disinfecting chamber to deliver a flow of ozone water directed towards at least the back and/or the palm of the inserted hand(s). Optionally, in some embodiment having a suitable deep disinfecting chamber, also the forearm(s) and the elbow(s) can be sanitized.

The water supply can be selected from a continuous water supply or a batch supply, but for most applications the water supply is simply tap water delivered to the ozone generator for producing the ozone water and running to the disinfecting chamber via a suitably arranged conduit. It might be preferred that the water delivered to the ozone generator is e.g. de-mineralized water, de-ionized water and/or filtered water.

The produced ozone water is delivered to the disinfecting chamber, optionally without any additional pumping means. So in a simple embodiment, purely due to the pressure of the water supply system ozone water can raise or run to the disinfecting chamber to be spread via the plurality of ozone water delivery openings over the inserted hand(s) in the operative mode of the apparatus.

The larger the port the larger the risk that dissolved ozone volatilises, thus the port is made as narrow as possible so that the disinfecting chamber is a cavity with the smallest possible access opening. The narrow port aids in preventing ozone evaporation, and the pressure of the water supply system serves to keep the ozone concentration in the ozone water at a substantially constant level during the sanitation cycle, thereby enabling standardisation of ozone delivery to the inserted at least one hand. The plurality of ozone water delivery openings serves like a manifold or a shower head to distribution and gentle application of ozone water around the inserted at least one hand in a confined space of the disinfecting chamber at a gentle ozone water pressure of between e.g. 0.5-3 bar. Admixture of air, such as in atomised ozone water, or in aerosols, may be less preferred for some operations. The air entrains ozone with the result that ozone to some extent can escape from the disinfecting chamber out of the port. The consequence is lack of control of ozone concentration and thus of standardisation, as well as increased ozone concentrations in the air outside the disinfecting chamber.

The above implementation comprises use of electrolytically produced ozone dissolved in water. This permits more ozone to be dissolved and therefore the resulting ozone concentration is higher than that achieved by other methods.

In a preferred embodiment the ozone water has a temperature below 37° C. when coming out of the plurality of openings. The lower said temperature is the better control of ozone concentration, and a temperature of below 30° C., alternatively below 25° C., may be preferred for most purposes, with a preferred temperature interval of between 10° C. to 22° C. in e.g. hospital environments. Even lower temperatures are possible, and tests can be performed to determine the temperature for the selected implementation use environment.

In a preferred embodiment the control means may comprise failure detection means and/or failure alerting means. Failure detection may include but is not limited to sensoring lack of water supply, malfunction of the ozone generator, deviations in temperature settings, deviations in ozone concentration, early removal of a hand in relation to a sanitation protocol, identification errors, etc. Failure alerting means may comprise a signal, such as a sound or light signal, a voice message, a displayed massage, any of which can be transmitted at the location of the apparatus directly to the user, and be transmitted to a central control means, for initiation of remedying the error and failure.

The disinfecting chamber has an outlet connected to a drain. Any ozone remaining in the ozone water after having been used for sanitisation is of no harm and can go directly into the drain, where it even can provide yet a disinfecting in the drain until the ozone eventually breaks down. Such ozone in the drain kills microorganisms in the drain and contributes to keeping the drain clean.

If the hands are physically dirty or greasy the apparatus of the present invention can preferably be used after the hands have been washed, e.g. with soap and tap water at any temperature of the user's choice. The sanitisation of the present invention then follows in a separate operation subsequent to handwashing.

Optionally, the chamber is further provided with at least one primer output of a primer supply, arranged to deliver a release from the at least one primer output arranged as regulated by the control means.

One purpose of this primer pre-treatment is to generate an advanced oxidation process during the ozone water treatment. A second purpose of the pre-treatment is to dissolve natural grease, oils or fat on the skin surface.

Advantageously, this embodiment of the invention facilitates priming of the hand across the skin surface, incorporating removal of fatty deposits and naturally occurring fatty substances, such as oils. This is supportive of the following ozone containing step, as the prime enhances the action of the ozone when the latter contacts already partially cleansed skin, allowing good wetting and consistency across the surface. This, in turn, results in an effective sanitisation with no local areas of more or less sanitisation effect.

Optionally, the release comprises a high pH wash, with a pH arranged >pH 7, more likely in a range between 8 and 12, more preferably in a range between 9 and 11, or a pH of around 10 or 10.5.

Advantageously, different pH values of the release have different results and effects. Some contaminants may be more easily removed with a substance of higher pH. Flexibility in the pH of choice allows for wider implementation of this embodiment of the invention. For the applications mentioned above, including hospitals, nursing homes etc., an optimal pH has been determined of 10 or 10.5.

Optionally, the discharge comprises ozone water with ozone concentration arranged between 2 to 50 PPM, or between 3 and 30 PPM, or between 5 and 20 PPM, or between 10 and 15 PPM, or around 12 PPM.

Advantageously, the concentration of ozone water is flexible and can be tailored to a specific implementation of the apparatus according to this embodiment of the invention. For the applications mentioned above, including hospitals, nursing homes etc., an optimal ozone concentration could, as an example be about 12 PPM in aqueous solution.

Optionally, the release and/or the discharge of ozone water is/are arranged to be effected in a single continuous event or in a plurality of pulses.

Advantageously, this allows tailoring of the sanitisation to specific implementations of the invention and to different process preferences.

As mentioned above the t least one primer output can for some implementation comprise a means, such as s nozzle, to produce micro droplets and/or a high frequency shaker and/or an atomiser as a supplement or alternative to the plurality of ozone water delivery openings Advantageously, this embodiment of the invention arranges delivery of discharge or release in a condition of a fine mist on the hand(s). Such delivery provides for an even coating of the hand(s), good wetting of the skin surface and extensive and comprehensive coverage.

Control of the ozone concentration requires an almost closed disinfecting chamber with a port that just allows entry of the at least one hand.

In another embodiment the ozone water is delivered in the form of droplets, however the preferred embodiment is a continuous gentle flow of ozone water running out of the ozone water delivery openings.

Ozone is a chemical, which requires careful handling and which is subject to regulation for its use and level of exposure. So for some installations wherein ozone water at the end of a sanitisation cycle cannot be used for disinfecting a drain, e.g. if special regulations apply for exhaust water, provisions for ensuring any excess ozone is catalysed and rendered harmless, for example at the end of the sanitisation cycle or step, can be provided in relation to any part of the apparatus and the surrounding environment,—thus where the presence of ozone is not favoured. The catalyst may comprise, but is not limited to, such substances as manganese dioxide, aluminium, carbon supported metal oxides, copper, chlorine coated fibres, carbon-iron aerosol particles, metal catalysts.

Optionally, the apparatus for hand sanitisation further comprises a towel dispenser arranged capable of providing a towel for drying the at least one hand. Advantageously, the use of a towel subsequent to the sanitisation step(s) improves skin comfort.

Optionally, the apparatus for hand sanitisation further comprises a signal device comprising light and/or sound and/or display and/or other signalling means arranged to draw the attention of the at least one user and/or provide information to the at least one user while the apparatus is in operation and/or when at least one sanitisation is complete.

Advantageously, communication of information to, or actively drawing the attention of, a user allows said user to engage fully with the sanitisation steps and protocol. Suitable provision also provides confirmation to the user that the sanitisation has been fully and successfully completed.

The apparatus may advantageously comprise at least one sensor adapted for detection of an entry and/or exit of the at least one hand into the disinfecting chamber, and optionally a timer arranged to cooperate with the at least one sensor to regulate a sanitisation timing of the at least one hand inserted in the disinfecting chamber. The timer starts and stops the sanitisation in response to readings by the at least one sensor of the presence or non-presence of the hand inside the disinfecting chamber.

The first and second plurality of ozone water delivery openings can be provided in any desirable and beneficial pattern, such as in a matrix or an array.

At least one of the first and second plurality of ozone water delivery openings are provided so that the individual openings of a plurality is spaced part along a manifold in form of one or more of a pipe or tubing, or are distributed over a diffuser plate, which are simple means to distribute a liquid flow.

The apparatus may further comprise a means for adjusting the flow direction of the ozone water delivery openings to ensure that all areas of an inserted hand at all times can be covered and subjected to uniform sprinkling.

The means for adjusting the flow direction of the ozone water delivery openings may advantageously be selected to continuously change the flow direction according to a given controlled flow regime. By continuously is within the context of the present invention meant both a stepwise change of discharge angle, as well as smooth constant movement and change of the discharge angle. The continuously change of the discharge angle may be reciprocating between a starting position and an end position, whereafter this reciprocating sequence is repeated as many times as decided by e.g. the control unit or a control programme, or by a manually actuatable stop means, e.g. a foot pedal or switch.

The means for adjusting the flow direction of the ozone water delivery openings may comprise a motor, e.g. a step motor or synchronous motor, for varying the discharge angle of at least one of the first and second plurality of ozone water delivery openings separately, or the manifold as a combined unit.

Guide plates or baffle plates arranged adjacent the first and second plurality of ozone water delivery openings may serve as an expedient extra means for guiding the ozone water towards the inserted hand.

According to an aspect of the invention, there is provided a method of hand sanitisation using the above-described apparatus. The method of hand sanitisation comprising the steps of:
recognising at least one user whose at least one hand is going to be sanitised,
sensing the introduction of the at least one hand in a port, suitable for insertion of at least one hand into a disinfecting chamber,
sanitising the at least one hand with a discharge from at least one ozone water output.

The method may further comprise one or more of the steps of
sensing the introduction of the at least one hand in the port,
timing at least one sanitising step to a set length of time,
storing data related to an end of a timing of at least one sanitising step and/or a timing of a sanitisation cycle and/or the at least one user.

A recognition device may give the possibility of securing access for specific users, for allowing the apparatus to be used in a specific way tailored to a specific user (e.g. by running certain sanitisation operations dependent on who is using the apparatus and thereby tailoring levels of sanitisation to certain applications) and for enabling the logging of the use of the apparatus by a specific user. The recognition device may operate based on identification of a fingerprint, an eye scan, a badge or other security device comprising some kind of machine readable pattern e.g. a barcode, or by a code input, or RFID Tags. Suitable detecting means are included in the recognition device to detect and verify the user and allocate the prescribed sanitisation protocol if any such is defined. In case the user is not recognised the apparatus will run a predetermined standard routine and log the data of this sanitisation to also make statistics on non-protocol users.

By means of among other things the timing aspect of this embodiment of the invention, an effective sanitisation protocol can be established, which comprises a disinfecting procedure implemented over an optimised and consistent timeframe for each user of the apparatus. The design of the port into the disinfecting chamber is another aspect that contributes to optimised use and correct positioning of the hands in relation to the ozone water delivery openings.

Advantageously, data storage allows a record to be kept of apparatus function and implementation. It also provides an opportunity for a database to be developed and/or subsequent data analysis to be performed. Such data may comprise specific machine use data, including data associated with an individual user, and various groups of users.

Optionally, the method includes one or more of the further steps of:
sanitising the at least one hand with a release from at least one primer output as a first prime and/or the step of,
drying the at least one hand by means of a towel after washing and/or the step of,
alerting a user to an end of a timing of at least one sanitising step and/or a timing of a sanitisation cycle.

One purpose of this primer pre-treatment is to generate an advanced oxidation process during the ozone water treatment. A second purpose of this primer pre-treatment is to dissolve natural grease, oils or fat on the skin surface.

Advantageously, this embodiment of the invention facilitates priming of the hand across the skin surface, incorporating removal of fatty deposits and naturally occurring fatty substances, such as oils. This is supportive of the following ozone containing step, as the primer may enhance the action of the ozone when the latter contacts already partially cleansed skin, allowing good wetting and consistency across the surface, and speeds up the action of ozone on the microorganisms. This, in turn, results in an effective sanitisation with no local areas of more or less sanitisation effect.

Advantageously, the use of a towel subsequent to the sanitisation step(s) improves skin comfort.

Advantageously, communication of information to, or actively drawing the attention of, a user allows said user to engage fully with the sanitisation steps and protocol. Suitable provision also provides confirmation to the user that the sanitisation has been fully and successfully completed. The information preferably includes information of how to position the hands inside the disinfecting chamber. Alternatively, the disinfecting chamber may have a structural interior design that encourages the user to take the correct position of the hands and/or prevent the user from incorrect orientation of the hands inside the disinfecting chamber.

According to an aspect of the present invention, there is provided a system for hand sanitisation, comprising an apparatus according to any of the embodiments as detailed above.

Advantageously, the system then benefits from all the advantages comprised in the various embodiments of the apparatus according to the present invention.

According to another aspect of the present invention, there is provided a software product recorded on machine-readable data storage media, wherein the software product is executable upon computing hardware for implementing a method pursuant to an aspect of the invention.

Advantageously, such an aspect facilitates transfer of methods according to embodiments of the present invention between different individual apparatus and also allows backup of said methods for security.

It will be appreciated that features of the invention are susceptible to being combined in any combination without departing from the scope of the invention as defined by the appended claims.

BRIEF DESCRIPTION OF THE FIGURES

Embodiments of the present invention will now be described, by way of example only, with reference to the following diagrams and figures wherein.

DESCRIPTION OF EMBODIMENTS OF THE INVENTION

Figure 1A:
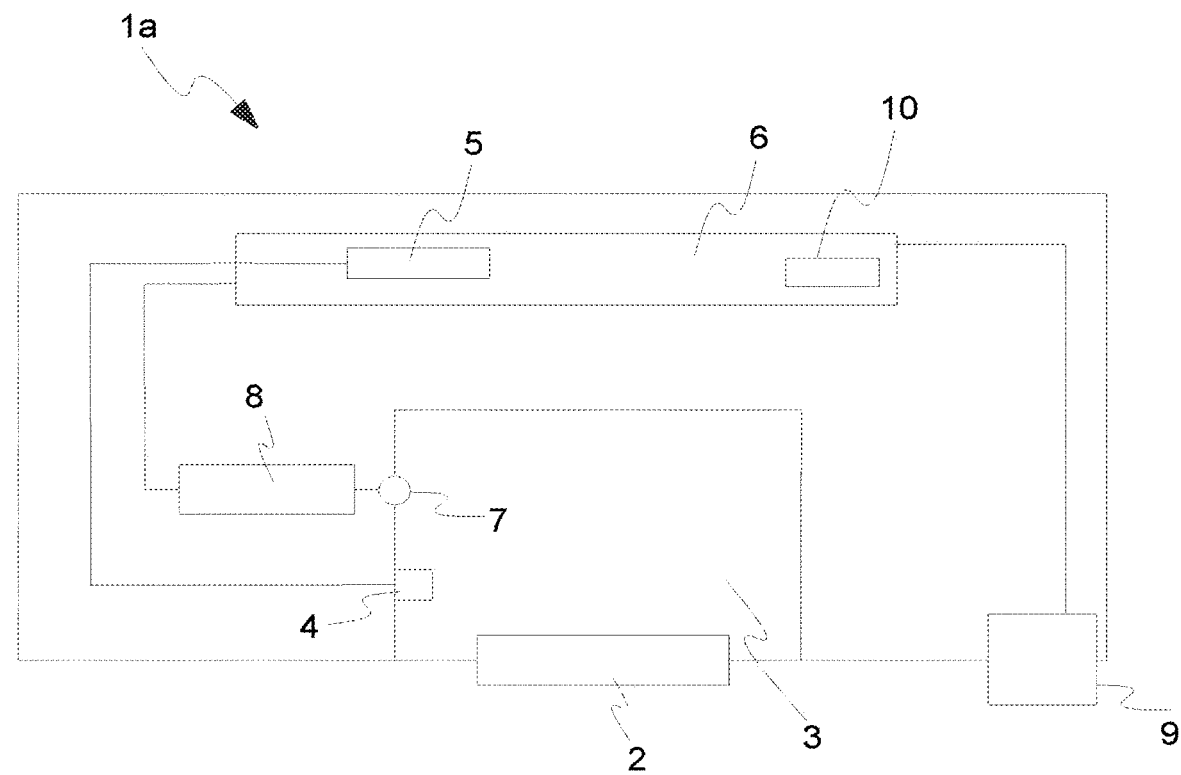
FIG. 1a is a schematic illustration of an apparatus according to a first embodiment of the present invention.

When describing embodiments of the invention, it will be appreciated that illustrations and figures are provided with reference to the sanitisation of hands. However, it is further envisaged that the invention can be applied more extensively, to forearms and elbows for example, with appropriate provision for the insertion of the forearms and elbows into the sanitising apparatus.

The apparatus shown in the drawing is as an example of a mobile unit, however the apparatus can quite as well be of a non-mobile kind, including be hung on a wall or be placed stationary on the floor in the vicinity of a receptacle for exhaust ozone water, e.g. a drain. The dimensions of the apparatus shown in the drawing and the positions of the various components should not be construed as limiting the scope of the presently claimed invention. The figures are given for illustrative purposes only.

The invention is intended for utilisation where a superior level of cleanliness is required or desired. For example, it is envisaged that the apparatus and method of the invention is applicable to medical applications, food production, or facilities serving the general public, such as catering or transport hubs. A particularly relevant area for the implementation of hand sanitation is a hospital. The various aspects and embodiments of the invention can be implemented at cleaning stations on wards or in ambulances, for example, where their use is directly effective in combating transmission of infection between patients. Another related example comprises implementation of embodiments of the invention in homes for the elderly or nursing homes.

Although the apparatus is described below in relation to hand disinfection is should be emphasized that also forearms and elbows can be disinfected. This is just a matter of structural design of the apparatus.

For the purposes of explanation, the terms sanitisation, disinfecting, washing etc. are used. It should be understood that these terms are used interchangeably to indicate a process, which beneficially affects the state of cleanliness of the skin. Use of the term sanitisation includes disinfecting and is not limited in the description below or above to the use of disinfecting materials or chemically defined disinfectants, rather the term is utilised to indicate a superior disinfection of the skin, comprising an effect which kills or removes pathogens, microorganisms etc.

In FIG. 1a, a schematically hand sanitisation apparatus is indicated generally by 1a. The hand sanitisation apparatus 1a comprises a port 2, suitable for insertion of at least one hand into a disinfecting chamber 3. The port 2 can be configured to accommodate more than one hand into the chamber 3, depending on the end application of the apparatus. The disinfecting chamber 3 is sized to optimise the application of any of a disinfecting step and/or a cleaning step onto the hand(s) while also permitting a limited flexibility of movement to prevent the hand(s) contacting the equipment and each other, or at least to limit said contact. The disinfecting chamber 3 is also provided with drainage and evacuation means for removal of spent cleaning materials—these features are not shown in the figure. The disinfecting chamber 3 is provided with a sensor 4, which is capable of detecting the introduction of one or more hands into the disinfecting chamber 3. The sensor 4 is input to a timer 5 arranged in association with a control means 6, which has primary control of the apparatus and implementation of various functions and timings. The timer 5 and control means 6 can be used to implement a desired step timing or cycle timing of the disinfecting process. The control means 6 is further arranged in association with at least one ozone water output 7, for regulation of a discharge from the ozone water output 7 as part of the hand sanitisation. Such a discharge may be arranged as a single continuous event, or in a plurality of pulses, which may be timed. The ozone water output 7 are provided in form of first plurality of ozone water delivery openings and a second plurality of ozone water delivery openings that forms the exit of an ozone water supply 8. The ozone water supply 8 comprises an electrolytic ozone generator (not shown) required to produce ozone water. The ozone water supply further comprises delivery means to bring the ozone water thus produced to the disinfecting chamber 3. The apparatus 1a further comprises a recognition device 9, which is arranged in association with the control means 6. This recognition device 9 allows a user to be identified, e.g. for the purpose of providing a targeted and specific sanitisation for that user, or for relation between data regarding the sanitisation and the user, or for security purposes to prevent unauthorised personnel from using the apparatus, among other options. In addition, the apparatus 1a comprises a means for storing data 10, comprised in the control means 6, which facilitates storage of e.g. user data, data from the sanitisation processes, and protocols for implementation of various sanitisations. Storing data related to a sanitisation cycle also permits the delivery of a test report in the event of apparatus failure and/or user manipulation.

Figure 1B:
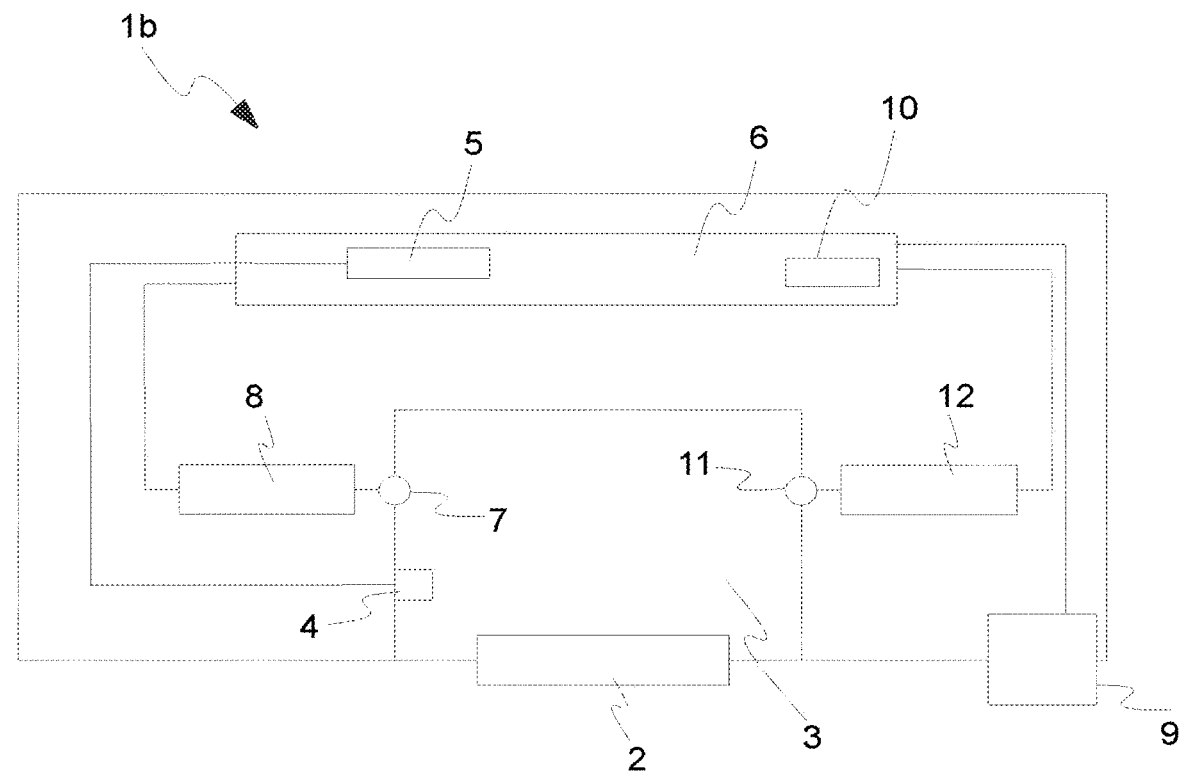
FIG. 1b is a schematic illustration of the apparatus of FIG. 1a comprising an additional feature, according to a further embodiment of the present invention.

In FIG. 1b, a schematically shown modified hand sanitisation apparatus is indicated generally by 1b. The hand sanitisation apparatus 1b comprises a port 2, suitable for insertion of at least one hand into a disinfecting chamber 3. The port 2 can be configured to accommodate more than one hand into the disinfecting chamber 3, depending on the end application of the apparatus. The purpose of the disinfecting chamber 3 is to locate the hand(s) to be sanitised. The disinfecting chamber 3 is sized to optimise the application of any disinfecting, washing or cleaning steps onto the hand(s) while also permitting some flexibility of movement to prevent the hand(s) contacting the equipment or each other, or at least to limit said contact. The disinfecting chamber 3 is also provided with drainage and evacuation means for removal of spent cleaning materials—these features are not shown in the figure. The disinfecting chamber 3 is provided with a sensor 4, which is capable of detecting the introduction of one or more hands into the disinfecting chamber 3.

The sensor 4 is input to a timer 5 arranged in association with a control means 6, which has primary control of the apparatus and implementation of various functions and timings. The timer 5 and control means 6 can be used to implement a desired step timing or cycle timing of the sterilisation process. The control means 6 is further arranged in association with at least one primer output 11 and at least one ozone water output 7, for regulation of a release from the primer output 11 and a discharge from the ozone water output 7 as part of the hand sanitisation. Such a release or discharge may be arranged as a single continuous event, or in a plurality of pulses, which may be timed. The primer output 11 is an exit of a primer supply 12, in which suitable materials (frequently comprising Chlorine (Cl) additives e.g. $ClO_2^-$, can be stored or produced and by means of which said materials can be brought to the disinfecting chamber 3. Similarly, the ozone water output 7, in form of the selected patterns of a first plurality of ozone water delivery openings and/or a second plurality of ozone water delivery openings, respectively, forms the exit of an ozone water supply 8. The ozone water supply 8 comprises means (not shown) required to produce or supply ozone, and delivery means to bring the ozone water thus produced to the disinfecting chamber 3. The apparatus 1b further comprises a recognition device 9, which is arranged in association with the control means 6. This recognition device 9 allows a user to be identified, e.g. for the purpose of providing a targeted and specific sanitisation for that user, or for relation between data regarding the sanitisation and the user, or for security purposes to prevent unauthorised personnel from using the apparatus, among other options. In addition, the apparatus 1b comprises a means for storing data 10, comprised in the control means 6, which facilitates storage of e.g. user data, data from the sanitisation processes and protocols for implementation of various sanitisations. Storing data related to a sanitisation cycle also permits the delivery of a test report in the event of apparatus failure and/or user manipulation.

The primer could also be called a 'prep-fluid' or a 'priming fluid', as the substance is introduced into the process in the initial stages before an ozone-containing step is effected. The primer dissolves natural grease on the hand, which enhances the effect of the subsequent ozone water treatment. Further, it promotes an advanced oxidation process during the ozone water treatment.

An associated water source, such as a container or direct connection to tap water, is not shown in the figure.

The primer output 11 and the ozone water output 7 may comprise different shapes and sizes according to the required sanitisation process. The positioning of the outputs 7a, 7b is flexible in accordance with the patterns of ozone water delivery openings within the disinfecting chamber 3, and may be adapted according to the implementation of the invention.

Preferably is the ozone water output 7 simply a plurality of openings provided as a pattern in a manifold or a sprinkler to gentle apply a mild flow of ozone water over the back and the palm of the user's hand. The manifold can be provided by a matrix or arrays of tubing, be holes as in a rose of a water jug, or be provided as a diffuser plate, or devices having similar properties.

Due to the patterns of plurality of openings the wetting of the hand(s) is consistent, and the sanitisation effect of the ozone water applied very effective, over the entire skin surface. The ozone step is the main step of the sanitisation.

The primer output 11 delivers a degreasing or primer chemical onto the hand(s). One of the purposes of this first step is to remove fatty deposits on the skin, including a normal skin coating of oily, fatty material. A subsequent step with ozone water is thereby rendered more effective. Ideally, the primer step comprises a wash with high pH water, i.e. a wash with a solution which is alkaline, i.e. pH >7, preferably with pH in the region of 8-12 and more preferably with a pH between 9 and 11. A pH of around 10 or 10.5 is considered optimal for the currently targeted applications. Such a highly alkaline solution, applied either as a liquid wash or in a mist, conditions the hand(s) to receive an ozone water application and affects the microorganisms to be even more receptive to the ozone water treatment.

The ozone water is obtained by use of an electrolytic ozone generator. A specific implementation of an embodiment of the invention is now detailed which utilises this device.

The ozone dissolved in the water is targeted to a concentration with an aim of providing safe sanitisation in e.g. less than one minute. In particular, a timing of between 5 and 60 seconds for an ozone wash step is desirable, with a preferred timing of around, or somewhat less than, 30 seconds considered optimal and 90 seconds the maximum. This is associated with the ozone concentrations described above.

The apparatus is arranged to provide a steady and controlled amount of ozone in the water over the full time period allocated to the ozone wash step. The ozone is dissolved in water, which together with the narrow port 2 further contributes to avoid the escape of ozone gas to the outside environment surrounding the disinfecting chamber 3, thereby keeping an even better control of ozone concentration in the ozone water. A removal of residual ozone, by known catalysis methods and materials, is suitable for inclusion in the present invention, but indeed optional.

The ozone wash is arranged within safe levels for normal use involving hand(s) or skin. The release from the primer output 11 comprises a high pH wash, with a pH arranged >pH 7, more likely in a range between 8 and 12, more preferably in a range between 9 and 11, or a pH of around 10 or 10.5. By calculation, a safe time for sanitisation can be established such that the determined percentage of cleaning achieved is deemed to be >1.0 Log or >2.0 Log or >3 Log for an extended period. A typical wash time of 30 seconds is considered sufficient for a 2.0 Log removal at an ozone concentration of about 12 PPM, highly advantageous in effect when compared with an alcohol wash, for example, even when the alcohol wash is carried out over a prolonged period. The optimal time for sanitisation depends on various factors. These parameters can be stored or programmed (e.g. as a protocol) into a means for storing data 10, located in the control means 6, for correct implementation of the sanitisation.

Figure 2:
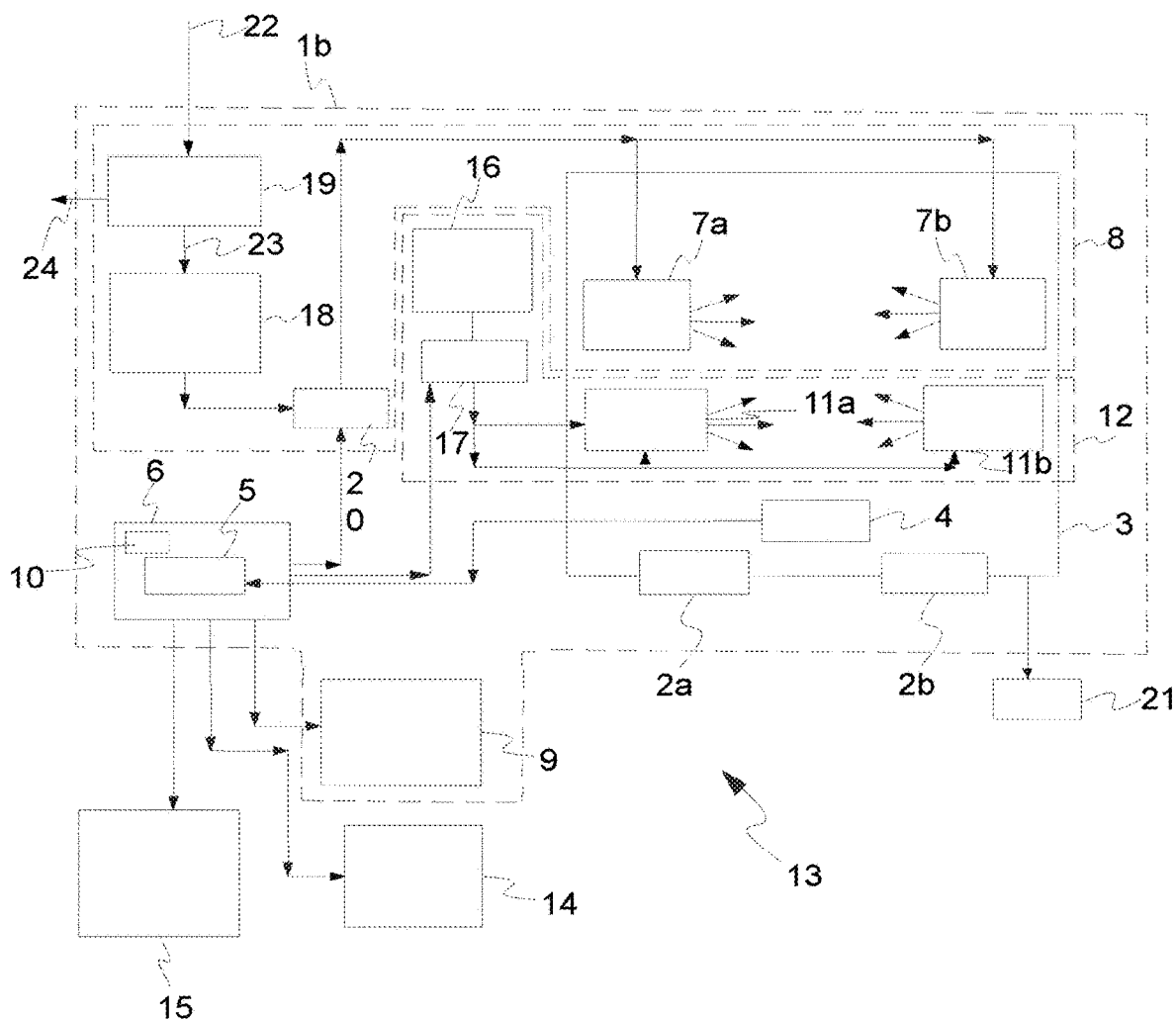
FIG. 2 is a schematic illustration of an apparatus according to a further embodiment of the present invention.

FIG. 2 shows a schematic illustration of an apparatus according to an embodiment of the present invention, wherein the apparatus of FIG. 1b is indicated by reference numeral 1b and other similar elements of this apparatus are labelled consistently in FIG. 2.

The schematic illustration of FIG. 2 shows a particular embodiment of the invention wherein the hand sanitisation apparatus 13 comprises the additional features of a towel dispenser 14 and a signal device 15, these additional features being arranged in cooperation with the control means 6, which activates each feature as necessary during the sanitisation process. (Each of the features may be comprised separately in other embodiments of the invention).

The towel dispenser 14 facilitates provision of a towel, which is used to dry the hand(s) after the ozone wash. The towel dispenser 14 is provided such that the towel is stored in a clean environment. By arrangement of the control means, a towel may be made available only when the complete sanitisation wash steps are finished according to a desired timing. This prevents short cutting of the sanitisation process.

Further, the apparatus comprises (user) recognition device 9, set-up to identify a user, either by a bar code or eye scan, for example. Successful registration of their data can be indicated.

The control means 6 further comprises means to record data on the sanitisation process, optionally in conjunction with the user information, and successful registration of the sanitisation data can be indicated.

In an embodiment of the apparatus of the present invention without recognition device 9 the user may have the option between various sanitisation programmes selectable via a user interface provided at the front of the apparatus of the present invention and controlled by the control means 6 to activate stored standard protocols of sanitisation. Standard protocols can include but is not limited to a selection of ozone steps, sanitisation times and ozone concentrations of the user's choice. The combinations and standard protocols may be pre-programmed factory setting or be created by a local of central manager as input to the control system.

A signal device 15, which may incorporate light, sound, display or other signalling means for drawing the attention of a user and/or providing information to a user while the apparatus is in operation, can be used to indicate to the user various stages of the process or the completion of the process. The user can thereby be notified e.g. of the end of each sanitisation process step, made aware of problems, required maintenance or malfunctions, or informed of the particular sanitisation running on the apparatus. The apparatus can be arranged to deliver a test report due to system failure and/or user manipulation. Optionally, the apparatus 13 may further comprise a separate indicator, not shown here, to announce to a user that the sanitisation process is at an end.

In the embodiment of FIG. 2, the apparatus 13 is shown to comprise two ports 2a, 2b each designed for insertion of one hand into the disinfecting chamber 3. Two optional primer outputs 11a, 11b are provided, arranged one on each side of the disinfecting chamber 3 such that each hand is supplied preferentially by one of the primer outputs 11a, 11b. Two schematically ozone water outputs 7a, 7b, one for each hand, are similarly arranged. Such a design facilitates equal sanitisation of both hands.

The two primer outputs 11a, 11b are comprised in the primer supply 12 which is shown here as further comprising a primer supply, preferably a high pH water supply 16 and a pump 17. The two primer outputs 11a, 11b of this embodiment preferentially comprise nozzles for formation of a steady stream of high pH water over the hands. In the figure, the pump 17 is shown as connected to the control means 6 and it is anticipated that activation of the pump 17 will produce an output. However, in a further embodiment of the invention, it is also possible to arrange the two primer outputs 11a, 11b under direct control of the control means 6.

The two ozone water outputs 7a, 7b are provided by the respective first plurality of ozone water delivery openings and are arranged as the first pattern selected to spread the ozone water over the palm of the inserted at least one hand, and as the second plurality of ozone water delivery openings arranged in the second pattern selected to spread the ozone water over the back of the inserted at least one hand, respectively, and are comprised in the ozone water supply 8.

The ozone water supply 8 is here illustrated as further comprising an electrolytic ozone generator 18, arranged to utilise a supply of ultra clean water supplied via a tap water filter device 19 used in the generation process and a valve 20 to facilitate the access of ozone water produced to the disinfecting chamber 3 by means of the ozone water outputs 7a, 7b. It is anticipated that activation of the electrolytic ozone generator 18 will produce an ozone output into the disinfecting chamber 3, however, in a further embodiment of the invention, it is also possible to arrange the two ozone water outputs 7a,7b under direct control of the control means 6.

The figure also illustrates that the disinfecting chamber 3 is connected to a drain 21, located external to the main apparatus 11. This provides for evacuation of excess liquid from the disinfecting chamber 3.

The tap water filter device 19 inputs tap water, illustrated by an arrow 22, and filters and otherwise treats the water so that ultra clean water is output, as illustrated by an arrow 23, and the residue, illustrated by an arrow 24, exits to a drain (not shown). The ultra clean water 23 is then input to the electrolytic ozone generator 18. Ultra clean water is in the context of the present application e.g. de-mineralized water, de-ionized water or filtered water, or combination of these.

Figure 3A:
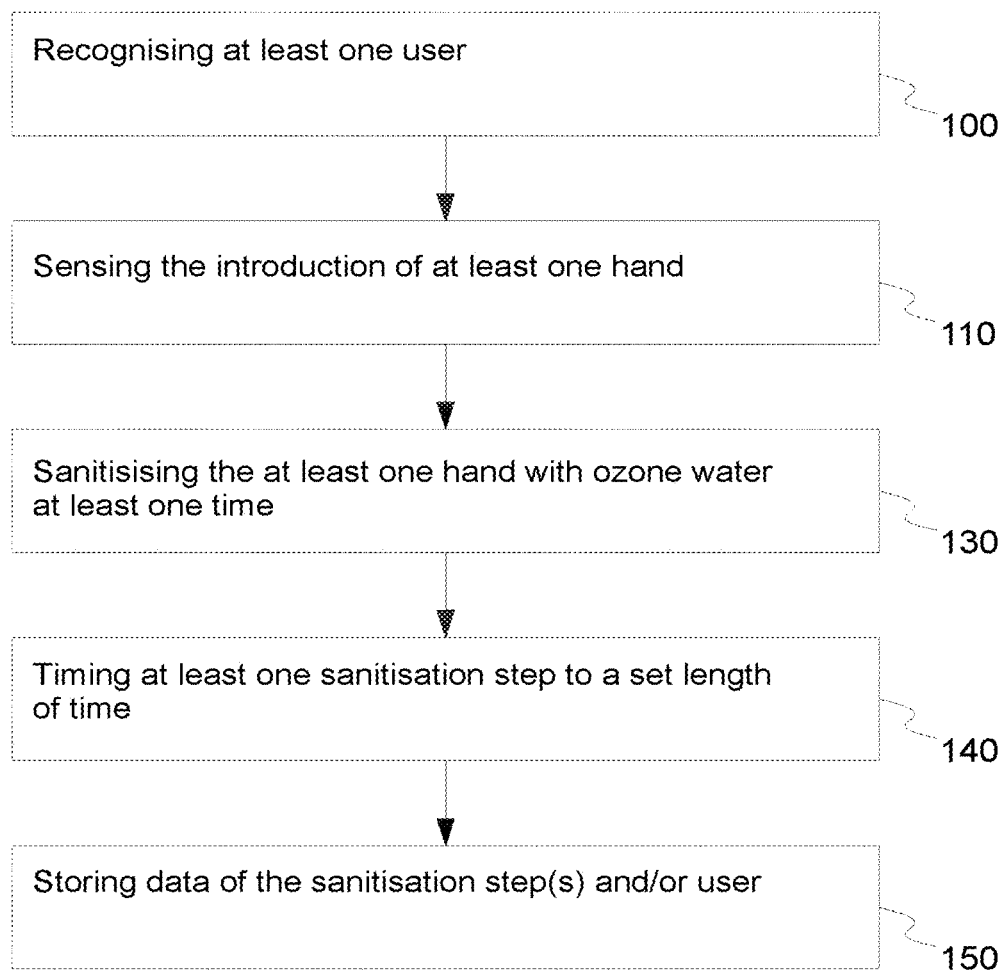
FIG. 3a is a schematic illustration of steps of a method of employing the apparatus of FIG. 1a in a hand sanitisation application.
Figure 3B:
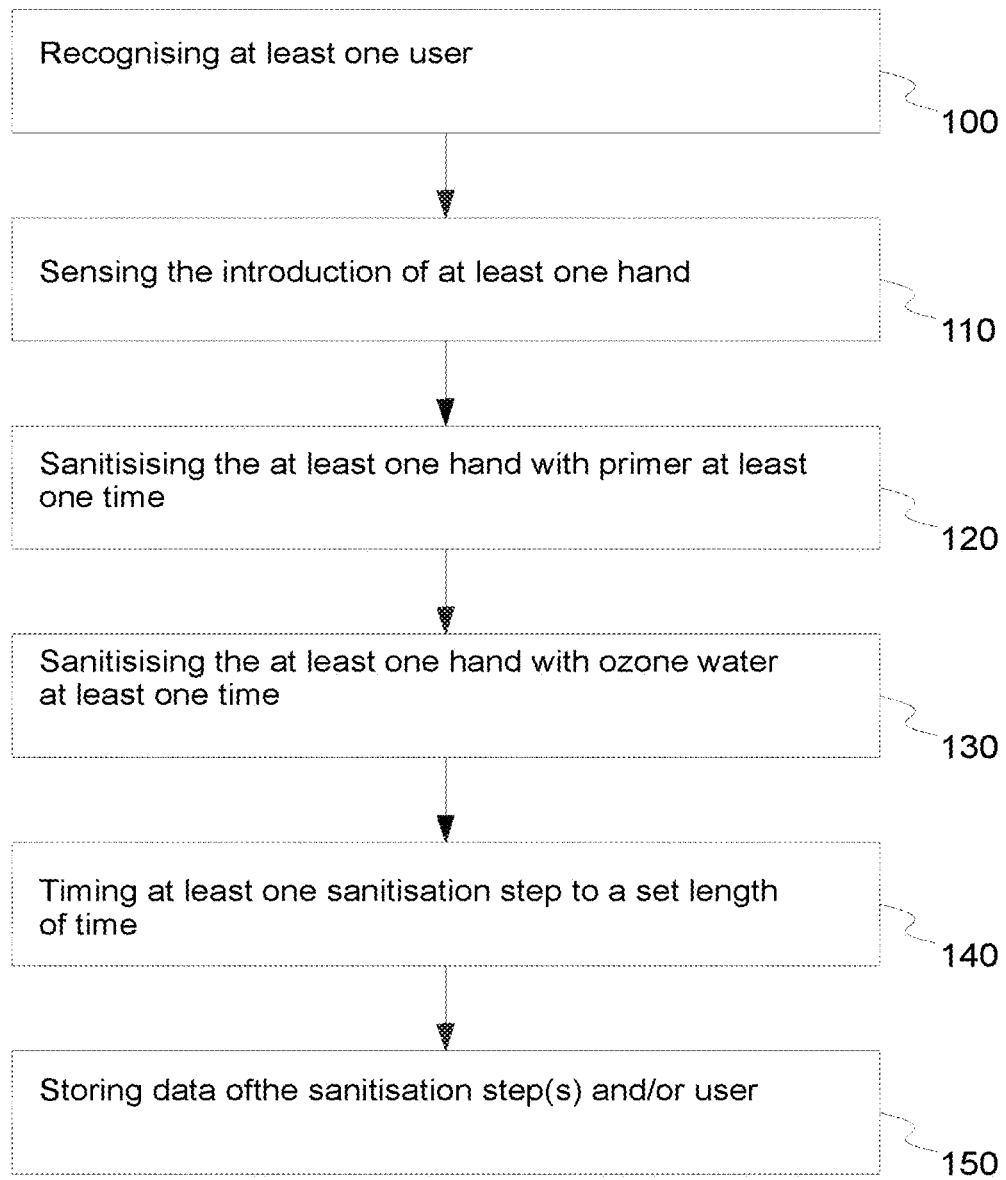
FIG. 3b is a schematic illustration of steps of a method of employing the apparatus of FIG. 1b in another hand sanitisation application.

FIG. 3a and FIG. 3b illustrate methods associated with embodiments of the present invention. Specifically, FIG. 3a relates to a method implemented by means of the apparatus la and FIG. 3b to a method implemented by apparatus 1b. As the method steps comprise steps in common, the figures will be described below in terms of the more extensive method associated with apparatus 1b.

Referring to FIG. 3b, the apparatus 1b implements an embodiment of the invention in a manner as defined by a method whose steps are illustrated in the figure.

The first method step 100 comprises recognising at least one user whose at least one hand is going to be sanitised. This step identifies the user whose hand(s) will be sanitised. This information is then available for the control means to be used during operation of the apparatus e.g. for protocol selection for a user so that a specific sanitisation is run for that user, or for identification of data generated in association with the user.

The second step 110 comprises sensing the introduction of the at least one hand in a port 2, suitable for insertion of at least one hand into a disinfecting chamber 3. This step ensures that a hand is present in the disinfecting chamber 3 for sanitisation and is related to the timing of the sanitisation steps as it acts as a baseline or start time, or depending on implementation, may act as the start trigger for the sanitisation process.

The third and optional method step 120 comprises sanitising the at least one hand with a release from at least one primer output as a first prime. This step can also be called a priming step. By performing this method step 120, the hand(s) are cleansed of e.g. grease, fatty deposits and fatty residue naturally present on the skin surface. Removal of these fatty substances prepares and conditions the hand(s) for the next step 130. Further the primer affects the microorganisms to make them more receptive of the ozone water treatment.

A fourth method step 130 comprises sanitising the at least one hand with a discharge from at least one ozone water output 7. The ozone in the water sanitises and thoroughly disinfects the hand surface. This step utilising ozone water can cover and wet the surface of the skin in a most efficient way due to the patterns of pluralities of ozone water delivery openings. A first prime step 120 can follow the ozone water step so that in some embodiments of use the skin is even more effectively sanitised. More than one prime step 120 can be implemented as desired. Similarly, more than one wash with ozone water 130 can be implemented as desired. Such multiple steps are not constrained to all prime steps being completed before one or more ozone washes are effected.

A fifth method step 140 comprises timing at least one sanitising step to a set length of time. By careful consideration of the strength and concentrations of the materials used, in conjunction with forethought regarding the degree of sanitisation required and the contamination likely to be eligible for removal, an optimum timing can be determined for each method step. This timing can then be implemented by the apparatus as an automatic procedure thereby ensuring a standardisation of method protocol and a consistency of application of the method of the invention between different users.

A sixth method step 150 comprises storing data related to an end of a timing of at least one sanitising step and/or a timing of a sanitisation cycle and/or the at least one user. Implementation of this method step allows for better management of the use of the apparatus and control of the sanitisation process. The user may be identified by means of a bar code or eye scan, for example. This allows specific logging of a user's activity on the apparatus.

Figure 4:
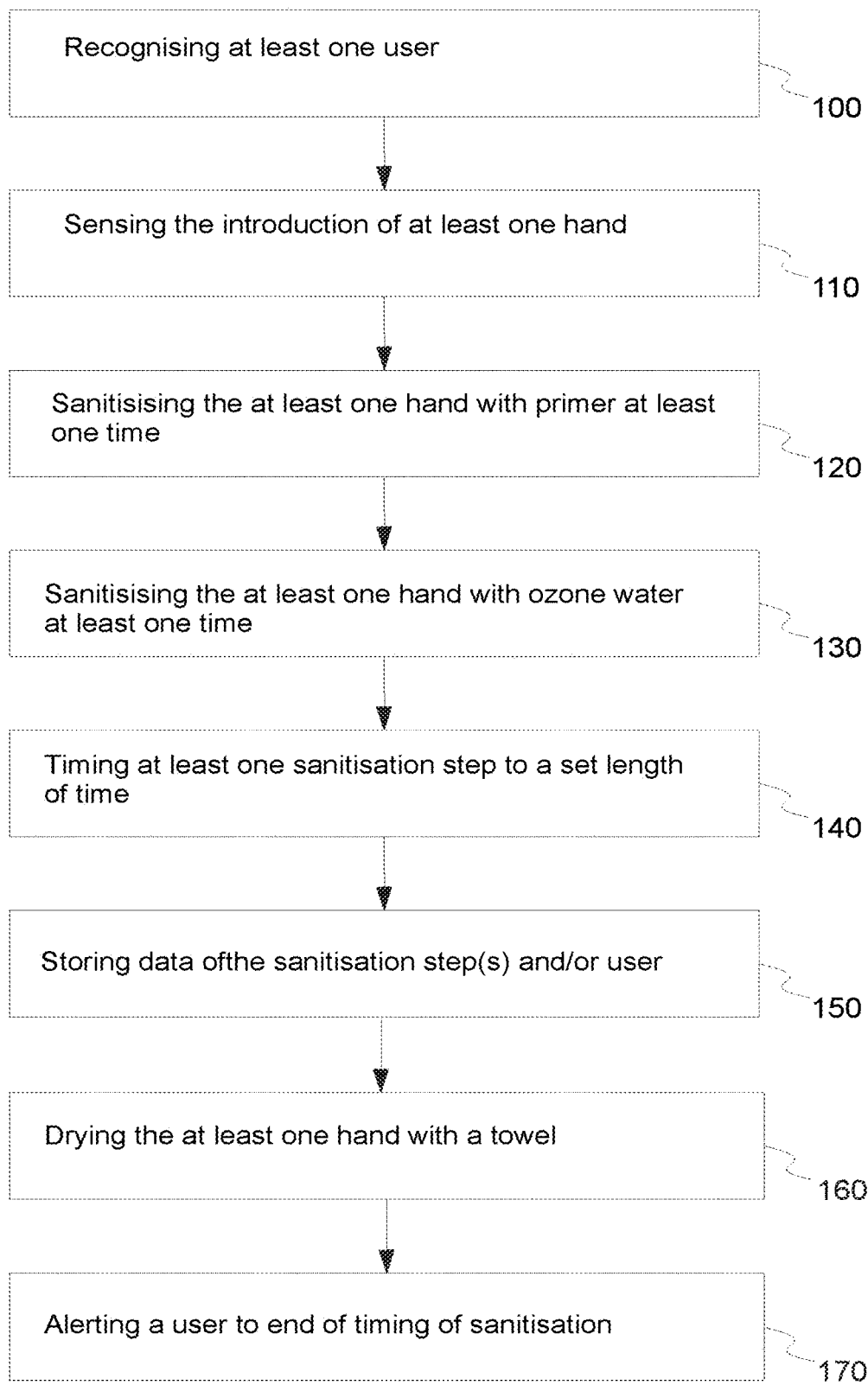
FIG. 4 is a schematic illustration of steps of a method of employing the apparatus of FIG. 2 in yet another hand sanitisation application.

Referring to FIG. 4, the apparatus 13 implements an embodiment of the invention in a manner as defined by a method whose steps are illustrated in the figure. This method incorporates steps 100, 110, 120, 130, 140, 150 of the previous method together with additional steps 160, 170. These additional steps 160, 170 are shown here as implemented together because the apparatus 13 is arranged to facilitate such use. However, the additional steps 160, 170 may be implemented individually, dependent on the set up of other apparatus according to a particular embodiment of the invention.

Method step 160 comprises drying the at least one hand by means of a towel after washing. By drying the hands, skin condition is protected. Use of a clean towel further reinforces the sanitisation process just accomplished by the sanitising steps, and indicates to the user that the sanitisation process is complete.

Method step 170 comprises alerting a user to an end of a timing of at least one sanitising step and/or a timing of a sanitisation cycle. This may be effected by various means depending on the circumstances and preferences of the user. A display may be used to chart the progress of the sanitisation and give information on the timing. A light indicator may be used to indicate completed process, e.g. a green light to indicate that the hands may be removed because the sanitisation cycle has been completed. Alternatively, a sound may be used, such a buzzer. This alert has advantages to the user as it provides confirmation that a full protocol is finished and it makes it more likely that the user will follow the protocol to the end, as there is anticipation of the confirmation by the user. The user is more engaged with the successful implementation of the sanitisation. Yet an alternative is that the delivery of ozone water to the hands simply stops at the end of the sanitisation protocol, which is an indication to the user to remove the hands and proceed to next step, e.g. drying the hands with the towel.

Figure 5:
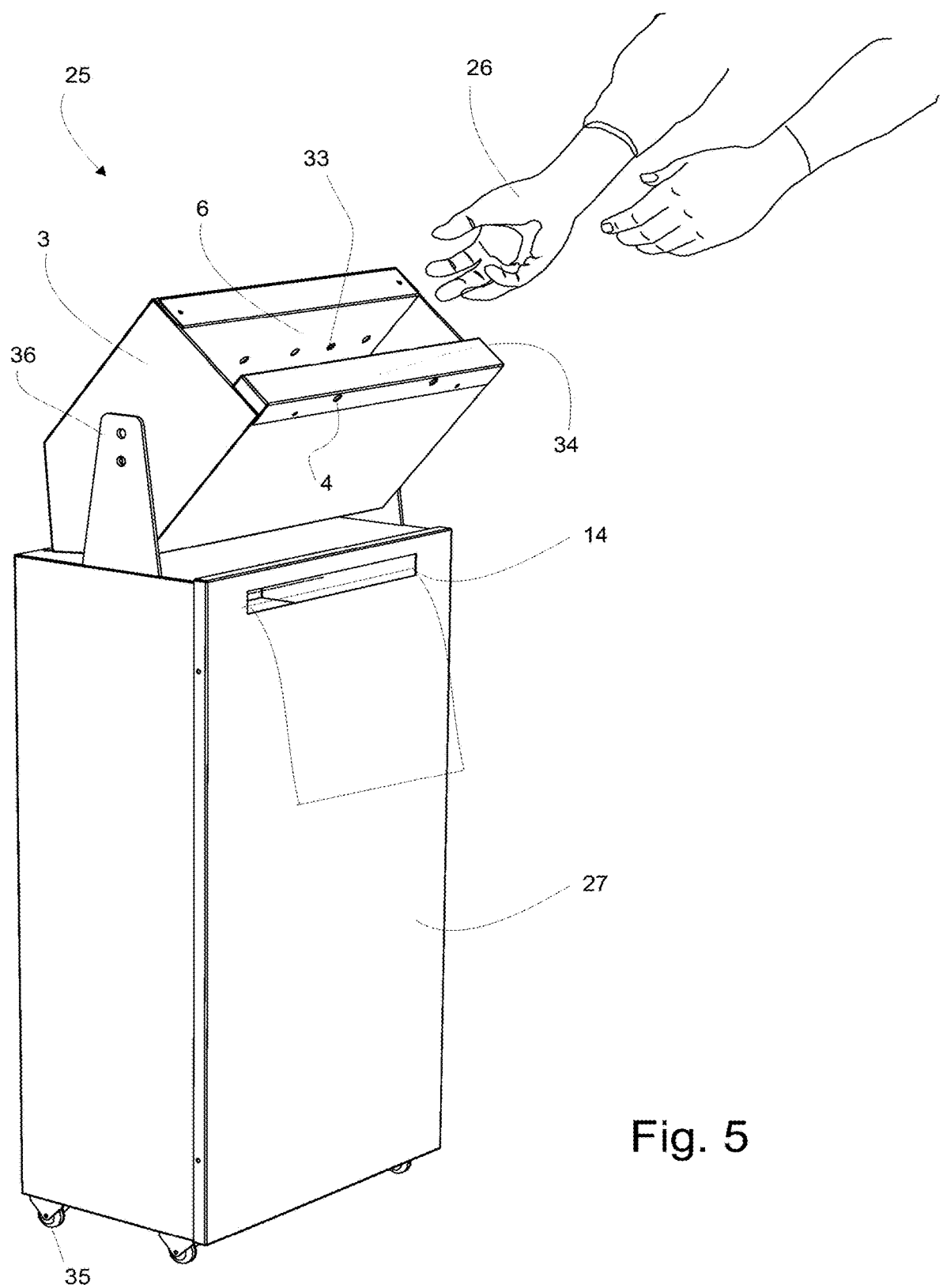
FIG. 5 is perspective view of an embodiment of an apparatus for hand sanitisation in accordance with the present invention with a user preparing to position the hands inside the disinfecting chamber.

FIG. 5 shows in perspective an exemplary design of a sanitisation apparatus 25, where a user is preparing for inserting his/her hands 26. Just prior to insertion of the hands 26 in the disinfecting chamber 3 the hands 26 are arranged in any of the positions seen in FIG. 6, wherein the hands are open and arranged flat next to each other and out of mutual contact. When the hands 26 are inside the disinfecting chamber 3 and the sanitisation protocol runs an optimum standardised disinfection takes place while the hands are kept in the same position during the timed sanitisation cycle and the ozone water gently runs over all areas of the hands 26. The sanitisation protocol decides the timer setting, the ozone concentration setting, the ozone water pressure setting, and the user is responsible for that the hands 26 are kept steady to allow the ozone water access to all corners and surfaces. The sanitisation protocol is determined by a user identification or the sanitisation protocol is run as a standard sanitisation protocol for an unknown user, or the sanitisation protocol is selected by the user via a user interface.

Figure 6:
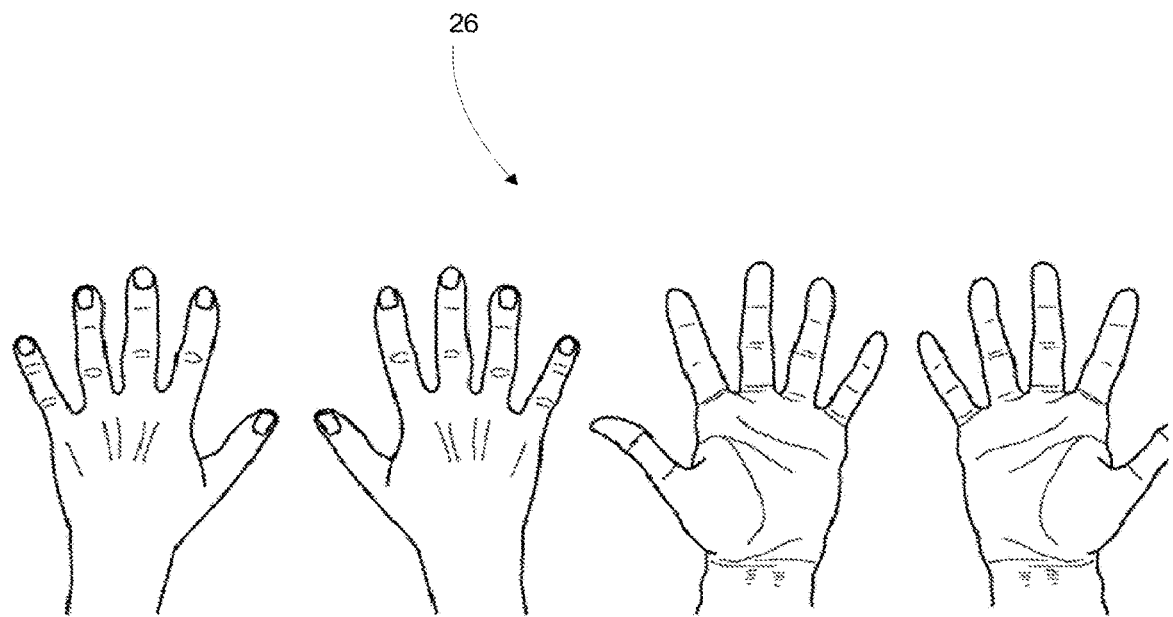
FIG. 6 illustrates suitable arrangements of a pair of hands when inserted into the disinfecting chamber via the port of the apparatus.
Figure 7:
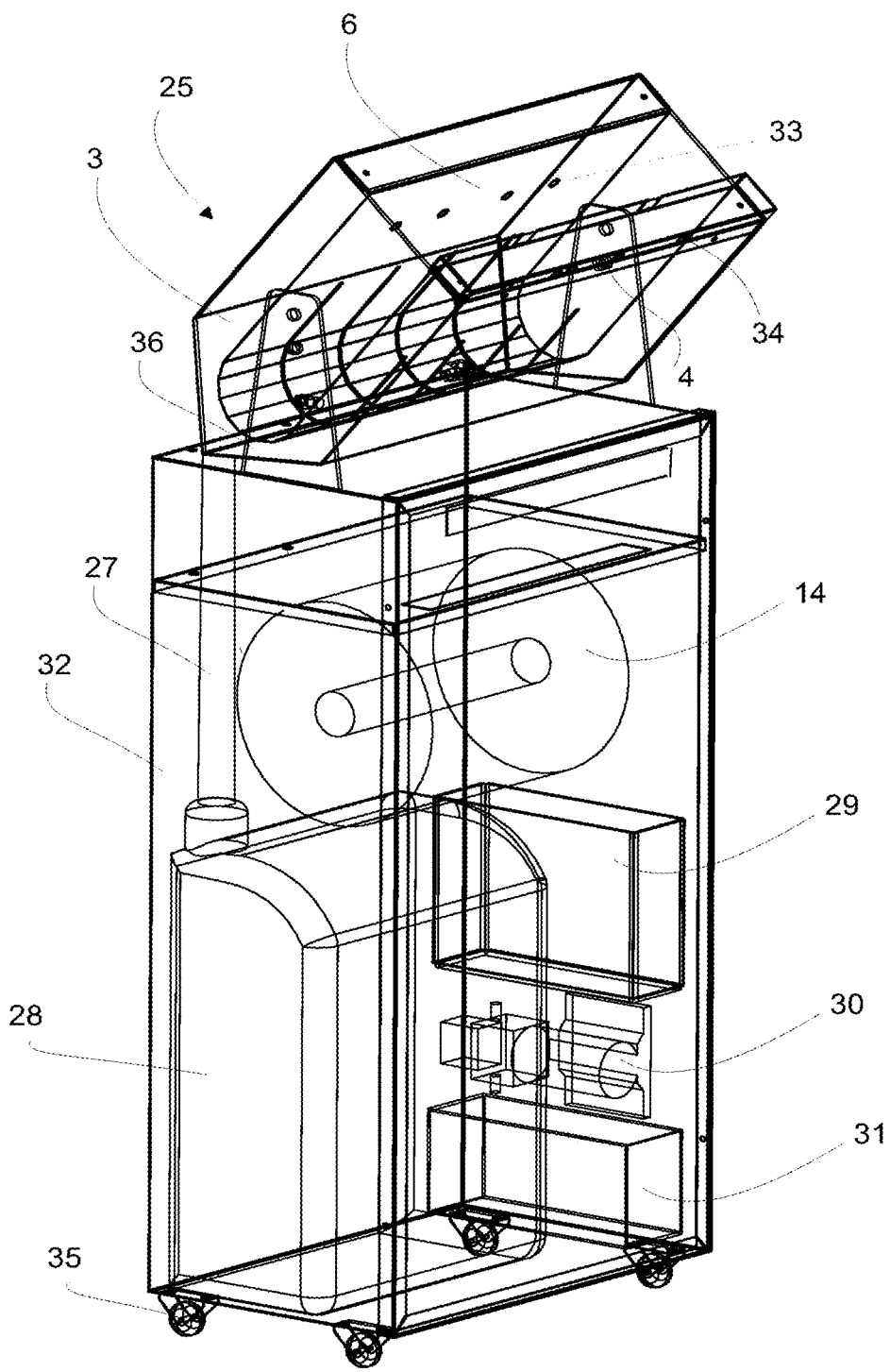
FIG. 7 shows the apparatus of FIG. 5 in transparent view to disclose the interior arrangement of the main components of the exemplary design of an apparatus for hand sanitisation.

As is clear from the transparent view of FIG. 7, the exemplary embodiment of a sanitisation apparatus 25 shown in FIG. 6 comprises a cabinet 27 that accommodates the ozone generator 28, a towel dispenser 14, a power box 29, a drain pump 30 and a drain tank 31 with an outlet or floor drain. The tap water supply to the ozone generator 28 and the power supply to the power box 29 are not shown in the figures.

Ozone water produced by the ozone generator 28 out of the tap water flows via ozone water conduit 32 to disinfecting chamber 3 with the ozone water output 7.

The ozone water output 7 is provided by a first plurality of ozone water delivery openings 33 arranged in a first pattern selected to spread the ozone water over the palm of the inserted hands (not shown), and/or a second plurality of ozone water delivery openings 34 arranged in a second pattern selected to spread the ozone water over the back of the inserted hands (not shown), or vice versa. For the purpose of overviewing the figure only a few of the pluralities of ozone water delivery openings 33, 34 are shown, as well as the patterns simply are shown as linear arrangements. It should be emphasised that the patterns can be any patterns suited to provide the flow, preferably a mild flow, to the hands 26 that are disinfected inside the disinfecting chamber 3. Patterns can be circular or special, e.g. similar to a hand with fingers spread and where the plurality of ozone water delivery openings 33, 34 are arranged corresponding to the hand contour above and below the respective hand. Thus the pattern of plurality of ozone water delivery openings above and below the left hand can be a mirror image of the pattern of plurality of ozone water delivery openings above and below the right hand.

The present exemplary of a sanitisation apparatus 25 has a disinfecting chamber 3 that can be tilted and locked into a position in which the port 2 is in an appropriate orientation for inserting the hands of users of different heights and abilities. For example, in an environment for users in wheel chairs or for children the port 2 must be kept low.

The means that allows the disinfecting chamber 3 to be locked in an angle in relation to the cabinet 27 are webs 36 arranged upright on the cabinet 27. The webs 36 are secured to the disinfecting chamber 3 in an appropriate angle by a suitable releasable fastening means, such as screws. Alternatively, the angle between the disinfecting chamber 3 and the cabinet 27 is fixed.

The cabinet 27 has wheels 35 to make the sanitisation apparatus 25 mobile. This means that the only requirement for use of the sanitisation apparatus 25 is access to water and a receptacle for wastewater. No soap or alcohol is needed incorporated in the apparatus, nor need the sanitisation apparatus be frequently replenished with disinfecting agents. The ozone water is produced on demand. The towel is an option and the sanitisation apparatus 25 may in some embodiments work even if the towel dispenser is run out. If the towel dispenser runs out this is registered by the control means and an alert is issued via the alerting means that replenishment is needed. Thus the sanitisation apparatus of the present invention is a very consistent product that requires minimum maintenance and provides a safe, reliable and highly disinfecting sanitisation regime for the user, optionally special sanitisation protocols for different known users or standard sanitisation protocols for known or unknown users.

Figure 8:
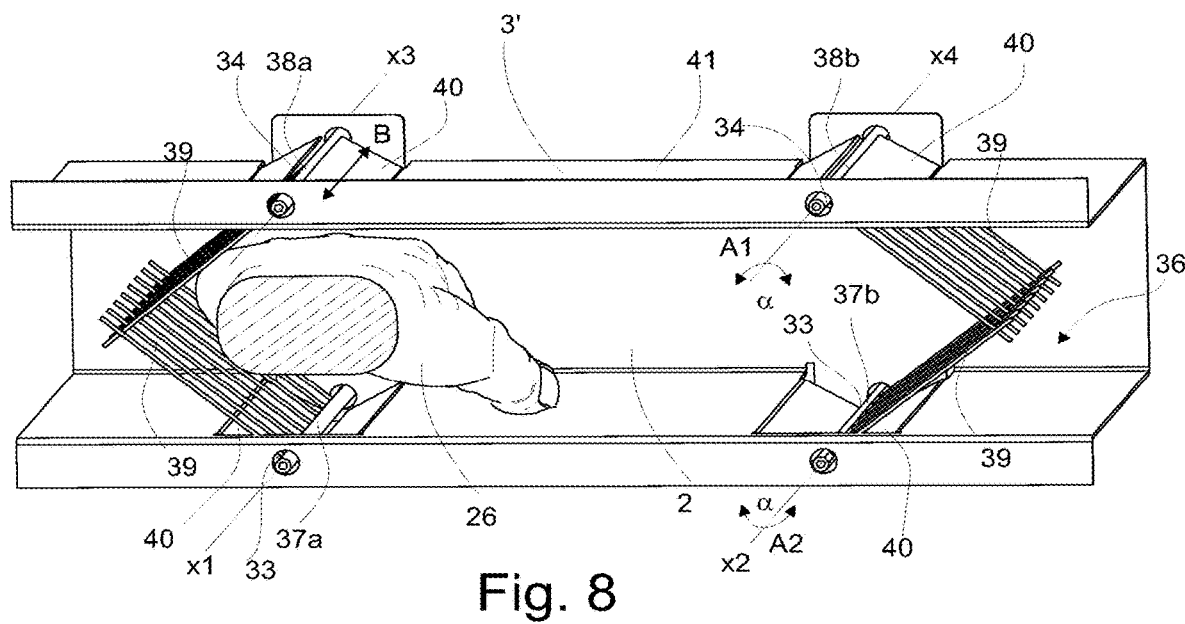
FIG. 8 shows a disinfecting chamber with an ozone water discharge arrangement in operation on one inserted left hand.

FIG. 8 shows a modified disinfecting chamber 3' with an ozone water discharge arrangement 36 operated by one or more motors (not shown).

In FIG. 8 the disinfection chamber 3' is seen from the front. The sides of the disinfection chamber 3' are not shown in FIG. 8 in order to visualize the interior structure of the ozone discharge arrangement 36.

The ozone water discharge arrangement 36 comprises two sets of pipes 37a,37b;38a,38b, the second set including the pipe 38a,38b above the inserted hand 26, and the first set including the pipes 37a,37b below the inserted hand 26, for varying the discharge angle α of an ozone water flow from at least one of the first and second plurality of ozone water delivery openings 33;34 individually, or of the manifold 36 as a combined unit, as indicated in FIG. 8 at double arrows A1 and A2.

The first set of pipes 37a,37b has a first plurality of ozone water delivery openings 33 and pivot the angle α about respective pipe axes x1,x2. The second set of pipes 38a,38b has the second plurality of ozone water delivery openings 34 and pivot the angle α about respective pipe axes x3,x4.

The pipes 37a,37b;38a,38b are pivoted back and forth within a discharge angle α of about 120°,—much like a garden sprinkler.

Further, within each complete angular pivoting cycle a pipe 37a,37b;38a,38b of the set of pipes can also be moved, as indicated by double arrow B in FIG. 8 at the left upper pipe second 38a, axially between a number of axial positions, such as fixed axial position. The spacing between said axial positions is small enough to ensure together with the angular movement of the pipes that the complete hand surface is covered by ozone water.

This way ozone water, that flows out of the pluralities of ozone delivery openings 33,34 as gentle, crossing streams 39, can in this design of a ozone water discharge arrangement be spread over an inserted hand 26 in a standardised manner.

Opposite plates 40 are arranged in V-shape along the pipes 37a,37;38a,38b on opposite sides of said pipes 37a, 37;38a,38b, so that the apices of the V-shape allow the pipes 37a,37;38a,38b to be slightly distanced from the wall 41 of the disinfecting chamber 3', this way giving more space for obtaining tapering of the discharge angle α without substantially increasing the interior available space for the hand 26, which space should be as narrow as possible to encourage the person using the disinfecting apparatus not to turn the hand during the disinfecting process. A further advantage is that the V-shape plates 40 may guide ozone water inside the chamber 3' at an angle limited by the legs of the V-shape. The V-shape plates 40 may thus also posses a baffle function.

Four pipes 37a,37;38a,38b are shown in in FIG. 8, but this number should not be construed as a limiting feature. Several additional pipes can be incorporated for altering the ozone water discharge pattern. The pipes has a plurality of equally spaced small holes serving as the first and second pluralities of ozone water delivery openings. Other spacing between the small holes are contemplated within the scope of the present invention. In the preferred embodiment the number of small holes, thus the number of first and second pluralities of ozone water delivery openings, respectively, multiplied by the spacing between said holes is substantially equivalent to the length of an average hand/wrist that is to be treated. All pipes 37a,37;38a,38b can be connected to the ozone generator by means of soft, bendable hoses.

Comparative Experiment

A prototype apparatus according to the present invention,—an Ozone Hand Disinfector with sprinkling ozone water dispensation —, was tested according to the below protocol to compare the disinfecting effect of the apparatus to conventional alcohol disinfection. A solution of bacteria including *Enterococcus* was prepared as basis for establishing the killing effect.

The hands of the test persons were washed with soap, rinsed with water in 2 min., and allowed to air-dry in 1 min. The bacteria solution was applied to the hands during 2×30 sec. Then the hands were again allowed to dry in the air for 3 min. Disinfection was conducted. 18 tests were conducted by three persons. The test were 6 references without disinfection, 6 tests using the Ozone Hand Disinfector with sprinkling water dispensation for 30 sec., and 6 comparative test using alcohol disinfection for 30 sec.

The experiments and calculations are conducted according to ASTM-2755-10 "StandardTest Method for Determining the Bacteria-Eliminating Effectiveness of Hand Sanitizer Formulations Using Hands of Adults". Alcohol disinfecting were conducted in six different hand rub positions according to the guidance set forth in EN1500 Clinical disinfectants and antiseptics—hygienic handrub—Test method and requirements.

Disinfecting in accordance with the present invention with ozone water followed the standardisation of the present invention wherein the hands are kept steady at the same position inside the disinfecting chamber, The conclusion is summarised in Table 1 below.

TABLE 1

| | | Bacterial reduction compared with reference | Standard Deviation |
|---|---|---|---|
| Ozone Hand Disinfector | Average | 99.73% | 0.21% |
| Alcohol disinfection | Average | 98.53% | 0.45% |
| | | Average (MPN/100 ml) | |
| References | | 798.600 | 78.602 |

The tests results forming the basis for the conclusion in Table 1 are presented in Table 2.

TABLE 2

| Test# | Serie # | Person | Test description | O3 conc. (PPM) | MPN/100 ml | Average Reference, (MPN/100 ml) | Percentage removal | Percentage removal (average Reference) |
|---|---|---|---|---|---|---|---|---|
| 1 | 1 | F | Ozone Hand Disinfector - 30 sec. | 20.9 | 1.000 | 798.600 | 99.88% | 99.87% |
| 4 | 1 | F | Reference | — | 860.000 | | x | x |
| 7 | 1 | F | Alcohol disinfection - 30 sec. | — | 10.900 | | 98.73% | 98.64% |
| 5 | 2 | V | Ozone Hand Disinfector - 30 sec. | 22.8 | 3.100 | | 99.62% | 99.61% |
| 2 | 2 | V | Reference | — | 813.000 | | x | x |
| 8 | 2 | V | Alcohol disinfection - 30 sec. | — | 12.100 | | 98.51% | 98.48% |
| 15 | 3 | L | Ozone Hand Disinfector - 30 sec. | 20.0 | 1.000 | | NA | 99.87% |
| 10 | 3 | L | Reference | — | NA* | | x | x |
| 12 | 3 | L | Alcohol disinfection - 30 sec. | — | 8.500 | | NA | 98.94% |
| 6 | 4 | F | Ozone Hand Disinfector - 30 sec. | 15.1 | 1.000 | | 99.86% | 99.87% |
| 3 | 4 | F | Reference | — | 733.000 | | x | x |
| 9 | 4 | F | Alcohol disinfection - 30 sec. | — | 6.300 | | 99.14% | 99.21% |
| 11 | 5 | V | Ozone Hand Disinfector - 30 sec. | 20.2 | 1.000 | | 99.86% | 99.87% |
| 14 | 5 | V | Reference | — | 703.000 | | x | x |
| 17 | 5 | V | Alcohol disinfection - 30 sec. | — | 14.600 | | 97.92% | 98.17% |
| 18 | 6 | L | Ozone Hand Disinfector - 30 sec. | 24.2 | 5.200 | | 99.41% | 99.35% |
| 13 | 6 | L | Reference | — | 884.000 | | x | x |
| 16 | 6 | L | Alcohol disinfection - 30 sec. | — | 14.600 | | 98.35% | 98.17% |

*NA: The reference in the third series (test # 10) could not be quantified due to a procedural error. Instead the average of the five other reference tests for calculation of values in series 3 were used.

The invention provides an easy platform for broad spectrum removal of various organisms, pathogens, spores, fungi and chemical impurities, even those as small as nanoparticles are within reach of the sanitisation. Liquids and other solid particles hazardous to health and detrimental to the quality of life are also susceptible to removal. So not only are microorganisms killed by the ozone present in the ozone water, the water removes killed microorganisms from the hands as well from the disinfecting chamber, and since the microorganisms are killed and the ozone suspended in the water, the entire sanitisation environment is extremely clean and safe to work and stay in. At the same time, consideration is given to the protection of the skin of the user by careful implementation.

By implementation of a method according to the invention a protocol is applied to the sanitisation process and the use of the apparatus can be monitored and data collected per user. Timing and implementation allow repeatable, equal, treatment of each user, a standardised sanitisation and a consistent result.

Although embodiments of the invention are described in the foregoing, it will be appreciated that the present invention is also susceptible to being implemented as a therapeutic apparatus, system and method. While the primary use of the apparatus is designed to be the sanitisation of hands, with a view to promoting cleanliness and the prevention of transmission of disease (and conditioning the hands to be suitable for use in applications where hygiene is of paramount importance), it is also envisaged that the apparatus may be used as a therapy to sanitise hands or other body parts where disease or contamination is already present to an amplified degree. The invention can either be implemented as presented or implemented with appropriate modifications for access of the body part to be treated, and for timing and concentrations of substances used.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The apparatus and the method according to the invention can make hand disinfection a uniform high quality, automated and well documented procedure. Thereby ensuring a standardization of method protocol and a consistency of application of the method between users. This secures compliance with the institution's policies.

The control means of the present invention may be configured to provide further advantageous control of operational status of the apparatus.

For example, in control mode A can predefined ranges of water flow through and from the ozone generator, limits of voltage, current and temperature be controlled and monitored by the control means. Registration by the control means that any of these parameters are outside its predefined range and/or level indicates malfunction and need for maintenance.

The control means can also include a module that facilitates and/or control proper user operation. For example, in a control mode B the sensors in the disinfecting chamber can verify that the user holds his/her hand(s) inside said disinfecting chamber until the entire disinfecting time and disinfecting cycle is completed.

Error messages and information can be issued by a reporting module associated with the control means to issue information to the user, or to the person or location responsible for maintenance.

If both control mode A and B are confirmed positive the message "Disinfection completed" will issue. If control mode A and/or B is not confirmed positive the message "ERROR", will issue. If control mode A, or both control mode A and control mode B cannot be verified positive the message "TECHNICAL ERROR—CALL SERVICE" will issue.

If control mode A but not control mode B is confirmed positive the message "INCOMPLETE DISINFECTION: USER ERROR" will issue, optionally with the added comment of "HANDS RETRACTED BEFORE DISINFECTION COMPLETE".

The issued alert, information or message of course depends on the occasioning situation and can be any entered text string, noise, moving or stationary image, pictogram, video, etc.

Data regarding the control mode can be stored and retrieved locally on and from, respectively, e.g. a USB storage.

Sending of data can take place via a computer network, intra network, or coupled to a server for operating a control programme of the control means. The control programme can be installed on the server and accessible via one or more PCs or be installed at the individual PCs.

The control programme and the control means may be adapted to issue data reports, alerts and warnings on a regular basis about apparatus quality, performance, and user operating errors, as well as coupling user data from a user log together with operating data from an operating log.

What is claimed is:

1. A method of hand sanitization comprising the steps of:
   providing an apparatus for sanitization of at least one hand by application of ozone water, the apparatus comprising,
   a disinfecting chamber having
     at least one port adapted for insertion of at least one hand into the disinfecting chamber,
     at least one sensor adapted for detection of an entry and/or exit of the at least one hand into the disinfecting chamber, and
     at least one ozone water output of the disinfecting chamber comprising a first plurality of ozone water delivery openings arranged in a first pattern selected to deliver and spread a continuous stream of ozone water over the palm of the at least one hand inside the disinfection chamber, and a second plurality of ozone water delivery openings arranged in a second pattern selected to deliver and spread a continuous stream of ozone water over the back of the inserted at least one hand,
   producing ozone water on demand by means of an ozone water supply that comprises an electrolytic ozone generator to obtain electrolytically produced ozone dissolved in water,
   sensing the introduction of the at least one hand through the at least one port, and starting a discharge of ozone water from the at least one ozone water output into the disinfecting chamber and delivering a continuous stream of ozone water to the palm and back of the at least one hand when said at least one hand is inserted into the disinfecting chamber,
   sanitizing the at least one hand with the discharge of ozone water from the at least one ozone water output, and
   stopping the discharge of ozone water from the at least one ozone water output in response to an input from a control means.

2. A method as claimed in claim 1 further comprising a step of recognising at least one user whose at least one hand is going to be sanitized.

3. A method as claimed in claim 2 wherein the step of recognising includes identification of a fingerprint, an eye scan, a badge or other security device comprising a machine readable pattern, a barcode, or a code input.

4. A method as claimed in claim 1 further comprising a step of timing at least one sanitizing step to a set length of sanitizing time.

5. A method as claimed in claim 4 further comprising a step of storing data related to an end of a timing of at least one sanitizing step and/or a timing of a sanitization cycle and/or the at least one user.

6. A method as claimed in claim 1 further comprising a step of drying the at least one hand by means of a towel after washing.

7. A method as claimed in claim 1 further comprising a step of alerting a user to an end of a timing of at least one sanitizing step and/or a timing of a sanitization cycle.

8. A method as claimed in claim 1 further comprising a step of washing the at least one hand with soap before sanitization with ozone water.

9. A method as claimed in claim 1 further comprising a step of storing data of at least one sanitization protocol arranged for the at least one user.

10. A method as claimed in claim 1 further comprising a step of customizing the at least one sanitization protocol to the individual user or to a group of users.

11. A method as claimed in claim 1 wherein the electrolytic ozone generator is connected to a water supply, the water supply being selected from a continuous water supply or a batch water supply.

12. A method as claimed in claim 1 further comprising a step of adjusting the temperature of the ozone water to below 30° C., or between 20° C. and 25° C.

13. A method as claimed in claim 1 further comprising draining used ozone water from the disinfecting chamber.

14. A method as claimed in claim 1 further comprising a step of detecting and alerting failures of the apparatus.

15. A method as claimed in claim 1, wherein the ozone water is discharged into the disinfecting chamber at an ozone concentration between 2 to 50 PPM, or between 3 and 30 PPM, or between 5 and 20 PPM, or between 10 and 15 PPM, or around 12 PPM.

16. A method as claimed in claim 1 further comprising a step of signaling information to the at least one user while the apparatus is in operation and/or when at least one sanitization is complete.

17. A method as claimed in claim 1 further comprising a step of adjusting the flow direction of the ozone water delivery openings.

18. A method as claimed in claim 17 wherein the step of adjusting the flow direction of the ozone water delivery openings is selected to continuously change the flow direction, preferably according to a given controlled flow regime.

19. A method as claimed in claim 17 wherein the step of adjusting the flow direction of the ozone water varies the discharge angle of at least one of the first and second plurality of ozone water delivery openings separately, or of a manifold as a combined unit.

20. A method as claimed in claim 1 wherein the ozone water is not admixed with air.

21. A method as claimed in claim 1 wherein the method further sanitizes at least one forearm, and at least one elbow, or combinations thereof.

22. A method as claimed in claim 1 wherein produced ozone water is delivered to the disinfecting chamber without any additional pumping means other than the pressure of a water supply system.

23. A method as claimed in claim 1 wherein produced ozone water is delivered to the disinfecting chamber due to the pressure of a water supply system.

24. A method as claimed in claim 1 wherein the step of sanitizing the at least one hand with a discharge of ozone water from the at least one ozone water output is for between 5 and 90 seconds.

25. A method as claimed in claim 1 wherein a determined percentage of bacterial kill achieved after the sanitization is >1.0 Log (90%) or >2.0 Log (99,0%) or >3 Log (99,9%).

26. A method as claimed in claim 1 wherein the electrolytic ozone generator utilizes a supply of de-mineralized water, de-ionized water or filtered water, or combination of these.

27. A method as claimed in claim 1 wherein the ozone water delivery openings gently distribute and apply ozone water around the inserted at least one hand at a gentle ozone water pressure of between 0.5 and 3 bar.

28. A method as claimed in claim 11 wherein the water supply is tap water.

29. A method as claimed in claim 1 wherein produced ozone water is delivered to the disinfecting chamber purely due to the pressure of the water supply system.

* * * * *